US012778786B2

(12) United States Patent
Mitchell et al.

(10) Patent No.: US 12,778,786 B2
(45) Date of Patent: Nov. 3, 2026

(54) SYSTEMS AND METHODS INCLUDING A MALE FLUID COLLECTION DEVICE AND A SECUREMENT ELEMENT

(71) Applicant: PureWick Corporation, El Cajon, CA (US)

(72) Inventors: Martyn Mitchell, Hertfordshire (GB); Leanne Yip Heung Win, Middlesex (GB); Samuel Edmund Whittome, Cambridge (GB); Ashley Marie Johannes, Statham, GA (US)

(73) Assignee: PUREWICK CORPORATION, Covington, GA (US)

( * ) Notice: Subject to any disclaimer, the term of this patent is extended or adjusted under 35 U.S.C. 154(b) by 0 days.

(21) Appl. No.: 17/446,256

(22) Filed: Aug. 27, 2021

(65) Prior Publication Data

US 2022/0062028 A1 Mar. 3, 2022

Related U.S. Application Data

(60) Provisional application No. 63/073,545, filed on Sep. 2, 2020.

(51) Int. Cl.

*A61F 5/453* (2006.01)
*A61F 5/44* (2006.01)
*A61F 5/443* (2006.01)

(52) U.S. Cl.

CPC ............ *A61F 5/453* (2013.01); *A61F 5/4405* (2013.01); *A61F 5/4408* (2013.01); *A61F 5/443* (2013.01)

(58) Field of Classification Search

CPC ....... A61F 5/453; A61F 5/4408; A61F 13/471
See application file for complete search history.

(56) References Cited

U.S. PATENT DOCUMENTS

| | | | |
|---|---|---|---|
| 670,602 | A | 3/1901 | Baker |
| 737,443 | A | 8/1903 | Mooers |
| 976,883 | A | 11/1910 | Keagy et al. |
| 1,015,905 | A | 1/1912 | Northrop |
| 1,032,841 | A | 7/1912 | Koenig |
| 1,178,644 | A | 4/1916 | Johnson |
| 1,229,423 | A | 6/1917 | Eckenrode |
| 1,387,726 | A | 8/1921 | Karge |
| 1,742,080 | A | 12/1929 | Jones |
| 1,979,899 | A | 11/1934 | Obrien et al. |

(Continued)

FOREIGN PATENT DOCUMENTS

| | | | |
|---|---|---|---|
| AU | 2018216821 | A1 | 8/2019 |
| AU | 2021299304 | A1 | 2/2023 |

(Continued)

OTHER PUBLICATIONS

US 9,908,683 B2, 03/2018, Tiesberger et al. (withdrawn)

(Continued)

*Primary Examiner* — Kai H Weng
*Assistant Examiner* — Katherine-Ph Minh Pham
(74) *Attorney, Agent, or Firm* — Ballard Spahr LLP

(57) ABSTRACT

Example male fluid collection devices and methods of collecting fluid are described. The fluid collection devices include a body defining a chamber sized to receive at least a head of a penis therein, one or more securement elements configured to secure the body to the penis, and a conduit in fluid communication with the chamber.

22 Claims, 11 Drawing Sheets

(56) References Cited

U.S. PATENT DOCUMENTS

| | | | |
|---|---|---|---|
| 2,241,010 | A | 5/1941 | Chipley |
| 2,262,772 | A | 11/1941 | Peder |
| 2,326,881 | A | 8/1943 | Packer |
| 2,379,346 | A | 6/1945 | Farrell |
| 2,485,555 | A | 10/1949 | Bester |
| 2,571,357 | A | 10/1951 | Charles |
| 2,613,670 | A | 10/1952 | Edward |
| 2,616,426 | A | 11/1952 | Adele |
| 2,644,234 | A | 7/1953 | Earl |
| 2,648,335 | A | 8/1953 | Chambers |
| 2,789,560 | A | 4/1957 | Weimer |
| 2,859,786 | A | 11/1958 | Tupper |
| 2,944,551 | A | 7/1960 | Carl |
| 2,968,046 | A | 1/1961 | Duke |
| 2,971,512 | A | 2/1961 | Reinhardt |
| 3,032,038 | A | 5/1962 | Swinn |
| 3,077,883 | A | 2/1963 | Hill |
| 3,087,938 | A | 4/1963 | Hans et al. |
| 3,114,916 | A | 12/1963 | Hadley |
| 3,169,528 | A | 2/1965 | Knox et al. |
| 3,171,506 | A | 3/1965 | Therkel |
| 3,175,719 | A | 3/1965 | Herndon |
| 3,194,238 | A | 7/1965 | Breece |
| 3,198,994 | A | 8/1965 | Hildebrandt et al. |
| 3,221,742 | A | 12/1965 | Egon |
| 3,312,221 | A | 4/1967 | Overment |
| 3,312,981 | A | 4/1967 | Mcguire et al. |
| 3,349,768 | A | 10/1967 | Keane |
| 3,356,091 | A | 12/1967 | Patterson |
| 3,362,590 | A | 1/1968 | Gene |
| 3,366,116 | A | 1/1968 | Huck |
| 3,368,564 | A | 2/1968 | Selix |
| 3,369,940 | A | 2/1968 | Slautterback |
| 3,398,848 | A | 8/1968 | Donovan |
| 3,400,717 | A | 9/1968 | Bruce et al. |
| 3,406,688 | A | 10/1968 | Bruce |
| 3,411,504 | A | 11/1968 | Glassman |
| 3,424,163 | A | 1/1969 | Gravdahl |
| 3,425,471 | A | 2/1969 | Yates |
| 3,434,565 | A | 3/1969 | Fischer |
| 3,447,536 | A | 6/1969 | Anna |
| 3,511,241 | A | 5/1970 | Lee |
| 3,512,185 | A | 5/1970 | Ellis |
| 3,520,300 | A | 7/1970 | Flower |
| 3,528,423 | A | 9/1970 | Lee |
| 3,608,552 | A | 9/1971 | Broerman |
| 3,613,123 | A | 10/1971 | Langstrom |
| 3,648,700 | A | 3/1972 | Warner |
| 3,651,810 | A | 3/1972 | Ormerod |
| 3,661,155 | A | 5/1972 | Lindan |
| 3,683,918 | A | 8/1972 | Pizzella |
| 3,699,815 | A | 10/1972 | Holbrook |
| 3,720,554 | A | 3/1973 | Stumpf |
| 3,721,243 | A | 3/1973 | Greth et al. |
| 3,726,277 | A | 4/1973 | Hirschman |
| 3,727,788 | A | 4/1973 | Holbrook |
| 3,730,411 | A | 5/1973 | Brockmuller |
| 3,742,952 | A | 7/1973 | Magers et al. |
| 3,742,953 | A | 7/1973 | Lee |
| 3,757,355 | A | 9/1973 | Allen et al. |
| 3,788,324 | A | 1/1974 | Lim |
| 3,843,016 | A | 10/1974 | Bornhorst et al. |
| 3,863,638 | A | 2/1975 | Rogers et al. |
| 3,863,798 | A | 2/1975 | Kurihara et al. |
| 3,864,759 | A | 2/1975 | Horiuchi |
| 3,865,109 | A | 2/1975 | Elmore et al. |
| 3,881,486 | A | 5/1975 | Fenton |
| 3,881,489 | A | 5/1975 | Hartwell |
| 3,915,189 | A | 10/1975 | Holbrook et al. |
| 3,931,650 | A | 1/1976 | Miller |
| 3,931,819 | A | 1/1976 | Weedle |
| 3,964,786 | A | 6/1976 | Mashuda |
| 3,998,228 | A | 12/1976 | Poidomani |
| 3,999,550 | A | 12/1976 | Martin |
| 4,006,793 | A | 2/1977 | Robinson |
| 4,015,604 | A | 4/1977 | Csillag |
| 4,020,843 | A | 5/1977 | Kanall |
| 4,022,211 | A | 5/1977 | Timmons et al. |
| 4,022,213 | A | 5/1977 | Stein |
| 4,023,216 | A | 5/1977 | Li |
| 4,027,776 | A | 6/1977 | Douglas |
| 4,031,897 | A | 6/1977 | Graetz |
| 4,042,337 | A | 8/1977 | Griffith |
| 4,064,962 | A | 12/1977 | Hunt |
| 4,069,817 | A | 1/1978 | Fenole et al. |
| 4,084,589 | A | 4/1978 | Kulvi |
| 4,096,897 | A | 6/1978 | Cammarata |
| 4,116,197 | A | 9/1978 | Bermingham |
| 4,140,739 | A | 2/1979 | Cotten |
| 4,180,178 | A | 12/1979 | Turner |
| 4,187,953 | A | 2/1980 | Turner |
| 4,194,508 | A | 3/1980 | Anderson |
| 4,197,849 | A | 4/1980 | Bostick |
| 4,200,102 | A | 4/1980 | Duhamel et al. |
| 4,202,058 | A | 5/1980 | Anderson |
| 4,203,503 | A | 5/1980 | Bertotti et al. |
| 4,209,076 | A | 6/1980 | Bertotti et al. |
| D255,935 | S | 7/1980 | Cullis et al. |
| 4,223,677 | A | 9/1980 | Anderson |
| 4,233,025 | A | 11/1980 | Larson et al. |
| 4,233,978 | A | 11/1980 | Hickey |
| 4,246,901 | A | 1/1981 | Frosch et al. |
| 4,253,542 | A | 3/1981 | Ruspa et al. |
| 4,257,418 | A | 3/1981 | Hessner |
| 4,270,539 | A | 6/1981 | Frosch et al. |
| 4,280,498 | A | 7/1981 | Jensen |
| 4,281,655 | A | 8/1981 | Terauchi |
| 4,292,916 | A | 10/1981 | Bradley et al. |
| 4,330,239 | A | 5/1982 | Gannaway |
| 4,345,341 | A | 8/1982 | Saito |
| 4,349,029 | A | 9/1982 | Mott |
| 4,352,356 | A | 10/1982 | Tong |
| 4,356,012 | A | 10/1982 | Hofstetter |
| 4,360,933 | A | 11/1982 | Kimura et al. |
| 4,365,363 | A | 12/1982 | Windauer |
| 4,372,299 | A | 2/1983 | Fixel |
| 4,375,841 | A | 3/1983 | Vielbig |
| 4,387,726 | A | 6/1983 | Denard |
| 4,403,991 | A | 9/1983 | Hill |
| 4,421,511 | A | 12/1983 | Steer et al. |
| 4,425,130 | A | 1/1984 | Desmarais |
| 4,446,986 | A | 5/1984 | Bowen et al. |
| 4,453,938 | A | 6/1984 | Brendling |
| 4,457,314 | A | 7/1984 | Knowles |
| 4,457,758 | A | 7/1984 | Norton |
| 4,476,879 | A | 10/1984 | Jackson |
| 4,512,771 | A | 4/1985 | Norton |
| 4,526,688 | A | 7/1985 | Schmidt et al. |
| 4,528,703 | A | 7/1985 | Kraus |
| 4,533,354 | A | 8/1985 | Jensen et al. |
| 4,533,357 | A | 8/1985 | Hall |
| D280,438 | S | 9/1985 | Wendt |
| 4,551,141 | A | 11/1985 | Mcneil |
| 4,553,968 | A | 11/1985 | Komis |
| 4,568,341 | A | 2/1986 | Mitchell et al. |
| 4,581,026 | A | 4/1986 | Schneider |
| 4,583,983 | A | 4/1986 | Einhorn et al. |
| 4,589,516 | A | 5/1986 | Inoue et al. |
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,572 | A | 7/1987 | Tokarz et al. |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |

(56) References Cited

U.S. PATENT DOCUMENTS 4,723,953 A 2/1988 Pratt et al.
4,735,841 A 4/1988 Sourdet
4,743,236 A 5/1988 Manschot
4,747,166 A 5/1988 Kuntz
4,752,944 A 6/1988 Conrads et al.
4,759,753 A 7/1988 Schneider et al.
4,769,215 A 9/1988 Ehrenkranz
4,771,484 A 9/1988 Mozell
4,772,280 A 9/1988 Rooyakkers
4,775,458 A 10/1988 Forester
4,784,654 A 11/1988 Beecher
4,790,830 A 12/1988 Hamacher
4,790,835 A 12/1988 Elias
4,791,686 A 12/1988 Taniguchi et al.
4,795,449 A 1/1989 Schneider et al.
4,798,603 A 1/1989 Meyer et al.
4,799,928 A 1/1989 Crowley
4,804,377 A 2/1989 Hanifl et al.
4,812,053 A 3/1989 Bhattacharjee
4,813,943 A 3/1989 Smith
4,820,291 A 4/1989 Terauchi et al.
4,820,297 A 4/1989 Kaufman et al.
4,841,728 A 6/1989 Jean et al.
4,846,818 A 7/1989 Keldahl et al.
4,846,819 A 7/1989 Welch
4,846,824 A 7/1989 Lassen et al.
4,846,909 A 7/1989 Klug et al.
4,857,064 A 8/1989 Mendoza
4,865,595 A 9/1989 Heyden
4,872,299 A 10/1989 Troutner et al.
4,875,898 A 10/1989 Eakin
4,880,417 A 11/1989 Yabrov et al.
4,882,794 A 11/1989 Stewart
4,883,465 A 11/1989 Brennan
4,886,498 A 12/1989 Newton
4,886,508 A 12/1989 Washington
4,886,509 A 12/1989 Mattsson
4,889,532 A 12/1989 Metz et al.
4,889,533 A 12/1989 Beecher
4,890,691 A 1/1990 Ching-Ho
4,895,140 A 1/1990 Bellak
4,903,254 A 2/1990 Haas
4,904,248 A 2/1990 Vaillancourt
D306,759 S 3/1990 D'Alo
4,905,692 A 3/1990 More
4,911,262 A 3/1990 Tani et al.
4,930,997 A 6/1990 Bennett
4,936,838 A 6/1990 Cross et al.
4,950,262 A 8/1990 Takagi
4,955,922 A 9/1990 Terauchi
4,957,487 A 9/1990 Gerow
4,965,460 A 10/1990 Tanaka et al.
4,986,823 A 1/1991 Anderson et al.
4,987,849 A 1/1991 Sherman
5,002,541 A 3/1991 Conkling et al.
5,004,463 A 4/1991 Nigay
5,013,308 A 5/1991 Sullivan et al.
5,030,229 A 7/1991 Yang
5,031,248 A 7/1991 Kemper
5,045,077 A 9/1991 Blake
5,045,283 A 9/1991 Patel
5,049,144 A 9/1991 Payton
5,053,339 A 10/1991 Patel
5,057,092 A 10/1991 Webster
5,058,088 A 10/1991 Haas et al.
5,071,347 A 12/1991 Mcguire
5,078,707 A 1/1992 Peter
5,084,037 A 1/1992 Barnett
5,100,396 A 3/1992 Zamierowski
5,102,404 A 4/1992 Goldberg et al.
5,112,324 A 5/1992 Wallace
5,134,994 A 8/1992 Say
5,137,033 A 8/1992 Norton
5,147,301 A 9/1992 Ruvio
5,176,667 A 1/1993 Debring
5,195,997 A 3/1993 Carns
5,196,654 A 3/1993 Diflora et al.
5,199,444 A 4/1993 Wheeler
5,203,699 A 4/1993 Mcguire
5,234,419 A 8/1993 Bryant et al.
5,244,458 A 9/1993 Takasu
5,246,454 A 9/1993 Peterson
5,267,988 A 12/1993 Farkas
5,275,307 A 1/1994 Freese
5,282,795 A 2/1994 Finney
5,294,983 A 3/1994 Ersoz et al.
5,295,979 A 3/1994 Delaurentis et al.
5,295,983 A 3/1994 Kubo
5,300,052 A 4/1994 Kubo
5,304,749 A 4/1994 Crandell
5,312,383 A 5/1994 Kubalak
5,318,550 A 6/1994 Cermak et al.
5,330,457 A 7/1994 Cohen
5,330,459 A 7/1994 Lavon et al.
5,334,174 A 8/1994 Street
5,334,176 A 8/1994 Buenger et al.
5,340,840 A 8/1994 Park et al.
D354,129 S 1/1995 Salvadori
D354,560 S 1/1995 Chase
5,382,244 A 1/1995 Telang
5,397,315 A 3/1995 Schmidt et al.
5,409,014 A 4/1995 Napoli et al.
5,409,475 A 4/1995 Steer
5,411,495 A 5/1995 Willingham
5,423,784 A 6/1995 Metz
5,423,788 A 6/1995 Rollins et al.
5,437,836 A 8/1995 Yamada
5,455,091 A 10/1995 Oreglia et al.
5,456,246 A 10/1995 Schmieding et al.
5,466,229 A 11/1995 Elson et al.
5,478,334 A 12/1995 Bernstein
5,499,977 A 3/1996 Marx
5,525,407 A 6/1996 Yang
5,543,042 A 8/1996 Filan et al.
D373,928 S 9/1996 Green
5,582,604 A 12/1996 Ahr et al.
5,592,950 A 1/1997 Kopelowicz
5,593,389 A * 1/1997 Chang .................. A61M 25/02
604/177
5,605,161 A 2/1997 Cross
5,614,699 A 3/1997 Yashiro et al.
5,618,277 A 4/1997 Goulter
5,628,735 A 5/1997 Skow
5,632,736 A 5/1997 Block
5,636,643 A 6/1997 Argenta et al.
5,637,104 A 6/1997 Ball et al.
D380,543 S 7/1997 Piontek et al.
5,662,633 A 9/1997 Doak et al.
5,674,212 A 10/1997 Osborn et al.
5,678,564 A 10/1997 Lawrence et al.
5,678,654 A 10/1997 Uzawa
5,681,297 A 10/1997 Hashimoto et al.
5,687,429 A 11/1997 Rahlff
5,695,485 A 12/1997 Duperret et al.
5,695,487 A 12/1997 Cohen et al.
5,700,254 A 12/1997 Mcdowall et al.
5,701,612 A 12/1997 Daneshvar
5,705,777 A 1/1998 Flanigan et al.
5,735,835 A 4/1998 Holland
5,735,837 A 4/1998 Ishikawa
5,752,944 A 5/1998 Dann et al.
5,763,333 A 6/1998 Suzuki et al.
5,772,644 A 6/1998 Bark et al.
5,792,132 A 8/1998 Garcia
5,827,243 A 10/1998 Palestrant
5,827,247 A 10/1998 Kay
5,827,250 A 10/1998 Fujioka et al.
5,827,257 A 10/1998 Fujioka et al.
D401,699 S 11/1998 Herchenbach et al.
5,859,393 A 1/1999 Cummins et al.
5,865,378 A 2/1999 Hollinshead et al.
5,873,869 A 2/1999 Hammons et al.
5,876,393 A 3/1999 Ahr et al.
5,887,291 A 3/1999 Bellizzi

(56) References Cited

U.S. PATENT DOCUMENTS 5,891,125 A 4/1999 Plumley
5,894,608 A 4/1999 Birbara
5,895,349 A 4/1999 Tihon
D409,303 S 5/1999 Oepping
5,911,222 A 6/1999 Lawrence et al.
5,956,782 A 9/1999 Olguin
5,957,904 A 9/1999 Holland
5,968,026 A 10/1999 Osborn et al.
5,972,505 A 10/1999 Phillips et al.
6,007,524 A 12/1999 Schneider
6,007,526 A * 12/1999 Passalaqua ............. A61F 5/453 604/352
D421,307 S 2/2000 Harmanoglu
6,039,060 A 3/2000 Rower
6,050,983 A 4/2000 Moore et al.
6,059,762 A 5/2000 Boyer et al.
6,061,905 A 5/2000 Logic
6,063,064 A 5/2000 Tuckey et al.
6,098,625 A 8/2000 Winkler
6,105,174 A 8/2000 Karlsten et al.
6,113,582 A 9/2000 Dwork
6,117,163 A 9/2000 Bierman
6,123,398 A 9/2000 Arai et al.
6,129,718 A 10/2000 Wada et al.
6,131,964 A 10/2000 Sareshwala
6,152,902 A 11/2000 Christian et al.
6,164,569 A 12/2000 Hollinshead et al.
6,177,606 B1 1/2001 Etheredge et al.
6,209,142 B1 4/2001 Mattsson et al.
6,220,050 B1 4/2001 Cooksey
6,244,311 B1 6/2001 Hand et al.
6,248,096 B1 6/2001 Dwork et al.
6,263,887 B1 7/2001 Dunn
6,283,246 B1 9/2001 Nishikawa
6,296,627 B1 10/2001 Edwards
6,311,339 B1 11/2001 Kraus
6,316,688 B1 11/2001 Hammons et al.
6,336,919 B1 1/2002 Davis et al.
6,338,729 B1 1/2002 Wada et al.
6,352,525 B1 3/2002 Wakabayashi
6,394,988 B1 5/2002 Hashimoto
6,395,956 B1 5/2002 Glasgow et al.
6,398,742 B1 6/2002 Kim
6,406,463 B1 6/2002 Brown
6,409,712 B1 6/2002 Dutari et al.
6,415,888 B2 7/2002 An et al.
6,416,500 B1 7/2002 Wada et al.
6,417,750 B1 7/2002 Sohn
6,423,045 B1 7/2002 Wise et al.
6,428,521 B1 8/2002 Droll
6,428,522 B1 8/2002 Dipalma et al.
6,446,454 B1 9/2002 Lee et al.
6,461,340 B1 10/2002 Lenker et al.
6,467,570 B1 10/2002 Herold
6,475,198 B1 11/2002 Lipman et al.
6,479,726 B1 11/2002 Cole et al.
6,491,673 B1 12/2002 Palumbo et al.
6,508,794 B1 1/2003 Palumbo et al.
6,524,292 B1 2/2003 Dipalma et al.
6,526,603 B1 3/2003 Murphy
6,540,729 B1 4/2003 Wada et al.
6,547,771 B2 4/2003 Robertson et al.
6,551,293 B1 4/2003 Mitchell
6,569,133 B2 5/2003 Cheng et al.
D476,518 S 7/2003 Doppelt
6,592,560 B2 7/2003 Snyder et al.
6,610,038 B1 8/2003 Dipalma et al.
6,618,868 B2 9/2003 Minnick
6,620,142 B1 9/2003 Flueckiger
6,629,651 B1 10/2003 Male et al.
6,635,037 B1 10/2003 Bennett
6,635,038 B2 10/2003 Scovel
6,652,495 B1 11/2003 Walker
6,666,850 B1 12/2003 Ahr et al.
6,685,684 B1 2/2004 Falconer
6,695,828 B1 2/2004 Dipalma et al.
6,699,174 B1 3/2004 Bennett
6,700,034 B1 3/2004 Lindsay et al.
6,702,793 B1 3/2004 Sweetser et al.
6,706,027 B2 3/2004 Harvie et al.
6,732,384 B2 5/2004 Scott
6,736,977 B1 5/2004 Hall et al.
6,740,066 B2 5/2004 Wolff et al.
6,764,477 B1 7/2004 Chen et al.
6,783,519 B2 8/2004 Samuelsson
6,796,974 B2 9/2004 Palumbo et al.
6,814,547 B2 11/2004 Childers et al.
6,848,719 B2 2/2005 Rowley
6,849,065 B2 2/2005 Schmidt et al.
6,857,137 B2 2/2005 Otto
6,878,647 B1 4/2005 Rezai et al.
6,885,690 B2 4/2005 Aggerstam et al.
6,888,044 B2 5/2005 Fell et al.
6,893,425 B2 5/2005 Dunn et al.
6,912,737 B2 7/2005 Ernest et al.
6,918,899 B2 7/2005 Harvie
6,979,324 B2 12/2005 Bybordi et al.
7,018,366 B2 3/2006 Easter
7,066,411 B2 6/2006 Male et al.
7,087,043 B2 * 8/2006 Dolan ..................... A61F 5/453 604/351
7,122,023 B1 10/2006 Hinoki
7,125,399 B2 10/2006 Miskie
7,131,964 B2 11/2006 Harvie
7,135,012 B2 11/2006 Harvie
7,141,043 B2 11/2006 Harvie
D533,972 S 12/2006 La
7,160,273 B2 1/2007 Greter et al.
7,166,092 B2 1/2007 Elson et al.
7,171,699 B2 2/2007 Ernest et al.
7,171,871 B2 2/2007 Kozak
7,179,951 B2 2/2007 Krishnaswamy-Mirle et al.
7,181,781 B1 2/2007 Trabold et al.
7,186,245 B1 3/2007 Cheng et al.
7,192,424 B2 3/2007 Cooper
7,219,764 B1 5/2007 Forbes
7,220,250 B2 5/2007 Suzuki et al.
D562,975 S 2/2008 Otto
7,335,189 B2 2/2008 Harvie
7,358,282 B2 4/2008 Krueger et al.
7,390,320 B2 6/2008 Machida et al.
7,438,706 B2 10/2008 Koizumi et al.
7,488,310 B2 2/2009 Yang
7,491,194 B1 2/2009 Oliwa
D591,106 S 4/2009 Dominique et al.
7,513,381 B2 4/2009 Heng et al.
7,520,872 B2 4/2009 Biggie et al.
D593,801 S 6/2009 Wilson et al.
7,540,364 B2 6/2009 Sanderson
7,549,511 B2 6/2009 Marocco
7,549,512 B2 6/2009 Newberry
7,585,293 B2 9/2009 Vermaak
7,588,560 B1 9/2009 Dunlop
7,637,905 B2 12/2009 Saadat et al.
7,658,730 B2 2/2010 Conley
7,665,359 B2 2/2010 Barber
7,682,347 B2 3/2010 Parks et al.
7,687,004 B2 3/2010 Allen
7,695,459 B2 4/2010 Gilbert et al.
7,695,460 B2 4/2010 Wada et al.
7,699,818 B2 4/2010 Gilbert
7,699,831 B2 4/2010 Bengtson et al.
7,722,584 B2 5/2010 Tanaka et al.
7,727,206 B2 6/2010 Gorres
7,740,620 B2 6/2010 Gilbert et al.
7,749,205 B2 7/2010 Tazoe et al.
7,755,497 B2 7/2010 Wada et al.
7,766,887 B2 8/2010 Burns et al.
7,803,144 B1 9/2010 Vollrath
D625,407 S 10/2010 Koizumi et al.
7,806,879 B2 10/2010 Brooks et al.
7,811,272 B2 10/2010 Lindsay et al.
7,815,067 B2 10/2010 Matsumoto et al.
7,833,169 B2 11/2010 Hannon

(56) References Cited

U.S. PATENT DOCUMENTS 7,857,806 B2 12/2010 Karpowicz et al.
7,866,942 B2 1/2011 Harvie
7,871,385 B2 1/2011 Levinson et al.
7,875,010 B2 1/2011 Frazier et al.
7,901,389 B2 3/2011 Mombrinie
7,927,320 B2 4/2011 Goldwasser et al.
7,927,321 B2 4/2011 Marland
7,931,634 B2 4/2011 Swiecicki et al.
7,939,706 B2 5/2011 Okabe et al.
7,946,443 B2 5/2011 Stull et al.
7,947,025 B2 5/2011 Buglino et al.
7,963,419 B2 6/2011 Burney et al.
7,976,519 B2 7/2011 Bubb et al.
7,981,087 B2 7/2011 Gesler, III
7,993,318 B2 8/2011 Olsson et al.
8,015,627 B2 9/2011 Baker et al.
8,016,071 B1 9/2011 Martinus et al.
8,028,460 B2 10/2011 Williams
8,047,398 B2 11/2011 Dimartino et al.
8,083,094 B2 12/2011 Caulfield et al.
8,128,608 B2 3/2012 Thevenin
8,156,941 B1 4/2012 Simms
8,167,860 B1 5/2012 Siegel
8,181,651 B2 5/2012 Pinel
8,181,819 B2 5/2012 Burney et al.
8,211,063 B2 7/2012 Bierman et al.
8,221,369 B2 7/2012 Parks et al.
8,241,262 B2 8/2012 Mahnensmith
8,277,426 B2 10/2012 Wilcox et al.
8,287,508 B1 10/2012 Sanchez
8,303,554 B2 11/2012 Tsai et al.
8,322,565 B2 12/2012 Caulfield et al.
8,337,477 B2 12/2012 Parks et al.
D674,241 S 1/2013 Bickert et al.
8,343,122 B2 1/2013 Gorres
8,343,125 B2 1/2013 Kawazoe et al.
8,353,074 B2 1/2013 Krebs
8,353,886 B2 1/2013 Bester et al.
D676,241 S 2/2013 Merrill
8,388,587 B1 3/2013 Gmuer et al.
8,388,588 B2 3/2013 Wada et al.
D679,807 S 4/2013 Burgess et al.
8,425,482 B2 4/2013 Khoubnazar
8,434,586 B2 5/2013 Pawelski et al.
8,449,510 B2 5/2013 Martini et al.
D684,260 S 6/2013 Lund et al.
8,470,230 B2 6/2013 Caulfield et al.
8,479,941 B2 7/2013 Matsumoto et al.
8,479,949 B2 7/2013 Henkel
8,500,719 B1 8/2013 Simpson et al.
8,512,301 B2 8/2013 Ma
8,529,530 B2 9/2013 Koch et al.
8,535,284 B2 9/2013 Joder et al.
8,546,639 B2 10/2013 Wada et al.
8,551,062 B2 10/2013 Kay
8,551,075 B2 10/2013 Bengtson
8,568,376 B2 10/2013 Delattre et al.
D694,404 S 11/2013 Burgess et al.
8,585,683 B2 11/2013 Bengtson et al.
8,586,583 B2 11/2013 Hamblin et al.
8,652,112 B2 2/2014 Johannison et al.
8,669,412 B2 3/2014 Fernkvist et al.
D702,973 S 4/2014 Norland et al.
8,702,667 B1 4/2014 Johnson
8,703,032 B2 4/2014 Menon et al.
D704,330 S 5/2014 Cicatelli
D704,510 S 5/2014 Mason et al.
D705,423 S 5/2014 Walsh Cutler
D705,926 S 5/2014 Burgess et al.
8,714,394 B2 5/2014 Wulf
8,715,267 B2 5/2014 Bengtson et al.
8,740,852 B2 6/2014 Aviles
8,757,425 B2 6/2014 Copeland
8,777,032 B2 7/2014 Biesecker et al.
8,808,260 B2 8/2014 Koch et al.
8,864,730 B2 10/2014 Conway et al.
8,881,923 B2 11/2014 Higginson
8,882,731 B2 11/2014 Suzuki et al.
8,936,585 B2 1/2015 Carson et al.
D729,581 S 5/2015 Boroski
9,028,460 B2 5/2015 Medeiros
9,056,698 B2 6/2015 Noer
9,078,792 B2 7/2015 Ruiz
9,145,879 B2 9/2015 Pirovano et al.
9,173,602 B2 11/2015 Gilbert
9,173,799 B2 11/2015 Tanimoto et al.
9,187,220 B2 11/2015 Biesecker et al.
9,199,772 B2 12/2015 Krippendorf
9,233,020 B2 1/2016 Matsumiya
9,248,058 B2 2/2016 Conway et al.
9,308,118 B1 4/2016 Dupree et al.
9,309,029 B2 4/2016 Incorvia et al.
9,333,281 B2 5/2016 Giezendanner et al.
9,381,108 B2 7/2016 Longoni et al.
9,382,047 B2 7/2016 Schmidtner et al.
9,402,424 B2 8/2016 Roy
9,415,191 B2 8/2016 Aviles
9,456,937 B2 10/2016 Ellis
9,480,595 B2 11/2016 Baham et al.
9,517,865 B2 12/2016 Albers et al.
D777,941 S 1/2017 Piramoon
9,533,806 B2 1/2017 Ding et al.
9,550,611 B2 1/2017 Hodge
9,555,930 B2 1/2017 Campbell et al.
9,623,159 B2 4/2017 Locke
D789,522 S 6/2017 Burgess et al.
9,687,849 B2 6/2017 Bruno et al.
9,694,949 B2 7/2017 Hendricks et al.
9,709,048 B2 7/2017 Kinjo
9,713,547 B2 7/2017 Lee et al.
9,732,754 B2 8/2017 Huang et al.
9,737,433 B2 8/2017 Joh
9,752,564 B2 9/2017 Arceno et al.
9,788,992 B2 10/2017 Harvie
D804,907 S 12/2017 Sandoval
D806,236 S 12/2017 Lin
9,868,564 B2 1/2018 Mcgirr et al.
D814,239 S 4/2018 Arora
D817,484 S 5/2018 Lafond
9,968,908 B2 5/2018 Ladrech et al.
10,010,393 B1 7/2018 Nguyen et al.
10,037,640 B2 7/2018 Gordon
10,058,470 B2 8/2018 Phillips
10,098,990 B2 10/2018 Koch et al.
D835,264 S 12/2018 Mozzicato et al.
D835,779 S 12/2018 Mozzicato et al.
D840,533 S 2/2019 Mozzicato et al.
D840,534 S 2/2019 Mozzicato et al.
10,225,376 B2 3/2019 Perez Martinez
10,226,376 B2 3/2019 Sanchez et al.
10,258,517 B1 4/2019 Maschino et al.
D848,612 S 5/2019 Mozzicato et al.
10,307,305 B1 6/2019 Hodges
10,335,121 B2 7/2019 Desai
D856,512 S 8/2019 Cowart et al.
10,376,406 B2 8/2019 Newton
10,376,407 B2 8/2019 Newton
10,390,989 B2 8/2019 Sanchez et al.
D858,144 S 9/2019 Fu
10,406,039 B2 9/2019 Villarreal
10,407,222 B2 9/2019 Allen
10,478,356 B2 11/2019 Griffin
10,500,108 B1 12/2019 Maschino et al.
10,502,198 B2 12/2019 Stumpf et al.
10,538,366 B2 1/2020 Pentelovitch et al.
10,569,938 B2 2/2020 Zhao et al.
10,577,156 B2 3/2020 Dagnelie et al.
RE47,930 E 4/2020 Cho
10,618,721 B2 4/2020 Vazin
D884,390 S 5/2020 Wang
10,669,079 B2 6/2020 Freedman et al.
D892,315 S 8/2020 Airy
10,730,672 B2 8/2020 Bertram et al.
10,737,848 B2 8/2020 Philip et al.

(56) References Cited

U.S. PATENT DOCUMENTS

| | | | |
|---|---|---|---|
| 10,765,854 | B2 | 9/2020 | Law et al. |
| 10,766,670 | B2 | 9/2020 | Kittmann |
| 10,799,386 | B1 | 10/2020 | Harrison |
| 10,806,623 | B2 | 10/2020 | VanMiddendorp et al. |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| 11,002,165 | B2 | 5/2021 | Poulin |
| D923,365 | S | 6/2021 | Wang |
| 11,020,567 | B2 | 6/2021 | Rule et al. |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,199,116 | B2 | 12/2021 | Ostromecki et al. |
| 11,207,206 | B2 | 12/2021 | Sharma et al. |
| D941,998 | S | 1/2022 | Tretheway et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,806,266 | B2 | 11/2023 | Sanchez et al. |
| 11,813,189 | B2 | 11/2023 | Hussey et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,890,221 | B2 | 2/2024 | Ulreich et al. |
| 11,911,160 | B2 | 2/2024 | Woodard et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| 12,048,644 | B2 | 7/2024 | Davis |
| D1,038,385 | S | 8/2024 | Ecklund et al. |
| 12,064,372 | B2 | 8/2024 | Godinez et al. |
| 12,070,432 | B2 | 8/2024 | Tourchak et al. |
| 12,090,083 | B2 | 9/2024 | Ecklund et al. |
| 12,121,468 | B2 | 10/2024 | Sanchez et al. |
| 12,133,813 | B2 | 11/2024 | Ulreich et al. |
| 12,138,195 | B2 | 11/2024 | Alder et al. |
| D1,054,019 | S | 12/2024 | Miyawaki |
| D1,059,585 | S | 1/2025 | Miyawaki |
| D1,059,586 | S | 1/2025 | Miyawaki |
| 12,186,229 | B2 | 1/2025 | Davis et al. |
| 12,193,962 | B2 | 1/2025 | Newton et al. |
| D1,067,424 | S | 3/2025 | Naughton et al. |
| 12,245,966 | B2 | 3/2025 | Newton |
| 12,274,638 | B2 | 4/2025 | Spector |
| D1,074,995 | S | 5/2025 | Laffay et al. |
| 12,324,765 | B2 | 6/2025 | Sanchez et al. |
| 12,350,190 | B2 | 7/2025 | Hughett, Sr. et al. |
| D1,104,255 | S | 12/2025 | Hanna et al. |
| D1,107,222 | S | 12/2025 | Ecklund et al. |
| 2001/0037097 | A1 | 11/2001 | Cheng et al. |
| 2001/0037098 | A1 | 11/2001 | Snyder |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0033200 | A1 | 3/2002 | Alex et al. |
| 2002/0042945 | A1 | 4/2002 | Sands |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2002/0193762 | A1 | 12/2002 | Suydam |
| 2003/0004436 | A1 | 1/2003 | Schmidt et al. |
| 2003/0018309 | A1 | 1/2003 | Breznock |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0074724 | A1 | 4/2003 | Sands |
| 2003/0120178 | A1 | 6/2003 | Heki |
| 2003/0129178 | A1 | 7/2003 | Wegman et al. |
| 2003/0157859 | A1 | 8/2003 | Ishikawa |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0002687 | A1 | 1/2004 | Burns et al. |
| 2004/0006321 | A1* | 1/2004 | Cheng .................... A61F 5/453 604/349 |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0098794 | A1 | 5/2004 | Ernest et al. |
| 2004/0102753 | A1 | 5/2004 | Butler |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |
| 2004/0147894 | A1 | 7/2004 | Mizutani et al. |
| 2004/0147895 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0181201 | A1 | 9/2004 | Mizutani et al. |
| 2004/0187200 | A1 | 9/2004 | Otto et al. |
| 2004/0191919 | A1 | 9/2004 | Unger et al. |
| 2004/0194792 | A1 | 10/2004 | Zhuang et al. |
| 2004/0200936 | A1 | 10/2004 | Opperthauser |
| 2004/0207530 | A1 | 10/2004 | Nielsen |
| 2004/0236292 | A1 | 11/2004 | Tazoe et al. |
| 2004/0243075 | A1 | 12/2004 | Harvie |
| 2004/0254547 | A1 | 12/2004 | Okabe et al. |
| 2005/0010182 | A1 | 1/2005 | Parks et al. |
| 2005/0010197 | A1 | 1/2005 | Lau et al. |
| 2005/0033248 | A1 | 2/2005 | Machida et al. |
| 2005/0065471 | A1 | 3/2005 | Kuntz |
| 2005/0070861 | A1 | 3/2005 | Okabe et al. |
| 2005/0070862 | A1 | 3/2005 | Tazoe et al. |
| 2005/0082300 | A1 | 4/2005 | Modrell et al. |
| 2005/0097662 | A1 | 5/2005 | Leimkuhler et al. |
| 2005/0101924 | A1 | 5/2005 | Elson et al. |
| 2005/0119630 | A1 | 6/2005 | Harvie |
| 2005/0131361 | A1 | 6/2005 | Miskie |
| 2005/0137557 | A1 | 6/2005 | Swiecicki et al. |
| 2005/0137560 | A1 | 6/2005 | Mizutani et al. |
| 2005/0137561 | A1 | 6/2005 | Mizutani et al. |
| 2005/0148984 | A1 | 7/2005 | Lindsay et al. |
| 2005/0154360 | A1 | 7/2005 | Harvie |
| 2005/0177070 | A1 | 8/2005 | Levinson et al. |
| 2005/0197639 | A1 | 9/2005 | Mombrinie |

(56) References Cited

U.S. PATENT DOCUMENTS

2005/0197645 A1 9/2005 Karpowicz et al.
2005/0215969 A1 9/2005 Mizutani et al.
2005/0273069 A1 12/2005 Mizutani et al.
2005/0273920 A1 12/2005 Marinas
2005/0277903 A1 12/2005 Mizutani et al.
2005/0277904 A1 12/2005 Chase et al.
2005/0279359 A1 12/2005 LeBlanc et al.
2006/0004332 A1 1/2006 Marx
2006/0005307 A1 1/2006 Arguelles
2006/0015080 A1 1/2006 Mahnensmith
2006/0015081 A1 1/2006 Suzuki et al.
2006/0016778 A1 1/2006 Park
2006/0069359 A1 3/2006 Dipalma et al.
2006/0079852 A1 4/2006 Bubb et al.
2006/0079854 A1 4/2006 Kay et al.
2006/0100596 A1 5/2006 Miskie
2006/0111648 A1 5/2006 Vermaak
2006/0113334 A1 6/2006 Mikhail et al.
2006/0155214 A1 7/2006 Wightman
2006/0166350 A1 7/2006 Lowe et al.
2006/0171997 A1 8/2006 Gruenbacher et al.
2006/0180566 A1 8/2006 Mataya
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1* 10/2006 Nan ....................... A61H 9/005
600/38
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0025886 A1 2/2007 Yong
2007/0038194 A1 2/2007 Wada et al.
2007/0055209 A1 3/2007 Patel et al.
2007/0073252 A1 3/2007 Forgrave
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1 9/2007 Carromba et al.
2007/0225663 A1 9/2007 Watt et al.
2007/0225666 A1 9/2007 Otto
2007/0225668 A1 9/2007 Otto
2007/0266486 A1 11/2007 Ramirez
2007/0270716 A1 11/2007 Wu et al.
2007/0282309 A1 12/2007 Bengtson et al.
2008/0004576 A1 1/2008 Tanaka et al.
2008/0015526 A1 1/2008 Reiner et al.
2008/0015527 A1 1/2008 House
2008/0033386 A1 2/2008 Okabe et al.
2008/0041869 A1 2/2008 Backaert
2008/0077099 A1 3/2008 House
2008/0091153 A1 4/2008 Harvie
2008/0091158 A1 4/2008 Yang
2008/0114327 A1 5/2008 Barge
2008/0140033 A1 6/2008 Burgess et al.
2008/0167634 A1 7/2008 Kouta et al.
2008/0183157 A1 7/2008 Walters
2008/0200884 A1 8/2008 Perkins et al.
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1 11/2008 Van Den Heuvel et al.
2008/0312550 A1 12/2008 Nishtala et al.
2009/0025717 A1 1/2009 Pinel
2009/0048570 A1* 2/2009 Jensen ................ B29C 45/0001
604/349
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0199857 A1 8/2009 Peake et al.
2009/0226541 A1 9/2009 Scholz et al.
2009/0234312 A1 9/2009 Otoole et al.
2009/0247968 A1 10/2009 Brooks et al.
2009/0251510 A1 10/2009 Noro et al.
2009/0254040 A1 10/2009 Bierman et al.
2009/0259206 A1 10/2009 Kai et al.
2009/0264840 A1 10/2009 Virginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0030189 A1 2/2010 Fleming
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0158168 A1 6/2010 Murthy et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.
2011/0087337 A1* 4/2011 Forsell .................. A61F 2/0036
600/38
2011/0145993 A1 6/2011 Rader et al.
2011/0152802 A1 6/2011 Dicamillo et al.
2011/0152842 A1 6/2011 Graffam et al.
2011/0164147 A1 7/2011 Takahashi et al.
2011/0172620 A1 7/2011 Khambatta
2011/0172625 A1 7/2011 Wada et al.
2011/0198904 A1 8/2011 Thomas et al.
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.
2011/0276020 A1 11/2011 Mitsui
2012/0004079 A1 1/2012 Hyacinth
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1 5/2012 Wheaton et al.
2012/0116336 A1 5/2012 Sharma et al.
2012/0137420 A1 6/2012 Gordon et al.
2012/0165768 A1 6/2012 Sekiyama et al.
2012/0165786 A1 6/2012 Chappa et al.
2012/0209216 A1 8/2012 Jensen et al.
2012/0209225 A1 8/2012 Hu et al.
2012/0210503 A1 8/2012 Anzivino et al.
2012/0215187 A1 8/2012 Tippet et al.
2012/0233761 A1 9/2012 Huang
2012/0245541 A1 9/2012 Suzuki et al.
2012/0245542 A1 9/2012 Suzuki et al.
2012/0245547 A1 9/2012 Wilcox et al.

(56) References Cited

U.S. PATENT DOCUMENTS

| | | | |
|---|---|---|---|
| 2012/0253303 | A1 | 10/2012 | Suzuki et al. |
| 2012/0271259 | A1 | 10/2012 | Ulert |
| 2012/0296305 | A1 | 11/2012 | Barraza Khaled et al. |
| 2012/0316522 | A1 | 12/2012 | Carter et al. |
| 2012/0330256 | A1 | 12/2012 | Wilcox et al. |
| 2013/0006206 | A1 | 1/2013 | Wada et al. |
| 2013/0019374 | A1 | 1/2013 | Schwartz |
| 2013/0036544 | A1 | 2/2013 | Lee et al. |
| 2013/0045651 | A1 | 2/2013 | Esteves et al. |
| 2013/0046258 | A1 | 2/2013 | Chambers |
| 2013/0053804 | A1 | 2/2013 | Soerensen et al. |
| 2013/0096523 | A1 | 4/2013 | Chang et al. |
| 2013/0110059 | A1 | 5/2013 | Kossow et al. |
| 2013/0138064 | A1 | 5/2013 | Stroebech et al. |
| 2013/0144240 | A1 | 6/2013 | Ellis |
| 2013/0150813 | A1 | 6/2013 | Gordon et al. |
| 2013/0158494 | A1 | 6/2013 | Ong et al. |
| 2013/0165880 | A1 | 6/2013 | Amos et al. |
| 2013/0211385 | A1 | 8/2013 | Lazarus |
| 2013/0218112 | A1 | 8/2013 | Thompson |
| 2013/0245496 | A1 | 9/2013 | Wells et al. |
| 2013/0245586 | A1 | 9/2013 | Jha |
| 2013/0274711 | A1 | 10/2013 | O'Day |
| 2013/0292537 | A1 | 11/2013 | Dirico |
| 2013/0324954 | A1 | 12/2013 | Friedrich |
| 2013/0330501 | A1 | 12/2013 | Aizenberg et al. |
| 2014/0005647 | A1 | 1/2014 | Shuffler et al. |
| 2014/0031774 | A1 | 1/2014 | Bengtson |
| 2014/0039432 | A1 | 2/2014 | Dunbar et al. |
| 2014/0039440 | A1 | 2/2014 | Doescher |
| 2014/0058347 | A1 | 2/2014 | Marquette |
| 2014/0107599 | A1 | 4/2014 | Fink et al. |
| 2014/0157499 | A1 | 6/2014 | Suzuki et al. |
| 2014/0171889 | A1 | 6/2014 | Hopman et al. |
| 2014/0182051 | A1 | 7/2014 | Tanimoto et al. |
| 2014/0196189 | A1 | 7/2014 | Lee et al. |
| 2014/0230831 | A1 | 8/2014 | Zaltsberg et al. |
| 2014/0257231 | A1 | 9/2014 | Wang et al. |
| 2014/0303582 | A1 | 10/2014 | Wright et al. |
| 2014/0316381 | A1 | 10/2014 | Reglin |
| 2014/0325746 | A1 | 11/2014 | Block |
| 2014/0348139 | A1 | 11/2014 | Gomez Martinez |
| 2014/0352050 | A1 | 12/2014 | Yao et al. |
| 2014/0371628 | A1 | 12/2014 | Desai |
| 2015/0045757 | A1 | 2/2015 | Lee et al. |
| 2015/0047114 | A1 | 2/2015 | Ramirez |
| 2015/0048089 | A1 | 2/2015 | Robertson |
| 2015/0135423 | A1 | 5/2015 | Sharpe et al. |
| 2015/0157300 | A1 | 6/2015 | Ealovega et al. |
| 2015/0209188 | A1 | 7/2015 | Scheremet et al. |
| 2015/0209194 | A1 | 7/2015 | Heyman |
| 2015/0267862 | A1 | 9/2015 | Mishler |
| 2015/0290421 | A1 | 10/2015 | Glickman et al. |
| 2015/0290425 | A1 | 10/2015 | Macy et al. |
| 2015/0320583 | A1 | 11/2015 | Harvie |
| 2015/0329255 | A1 | 11/2015 | Rzepecki |
| 2015/0342799 | A1 | 12/2015 | Michiels et al. |
| 2015/0359660 | A1 | 12/2015 | Harvie |
| 2015/0359996 | A1 | 12/2015 | Arora et al. |
| 2015/0366699 | A1 | 12/2015 | Nelson |
| 2015/0374535 | A1 | 12/2015 | Davis et al. |
| 2016/0008193 | A1 | 1/2016 | Schulke |
| 2016/0029998 | A1 | 2/2016 | Brister et al. |
| 2016/0030228 | A1 | 2/2016 | Jones |
| 2016/0038356 | A1 | 2/2016 | Yao et al. |
| 2016/0051395 | A1 | 2/2016 | Ugarte |
| 2016/0058322 | A1 | 3/2016 | Brister et al. |
| 2016/0060001 | A1 | 3/2016 | Wada et al. |
| 2016/0100976 | A1 | 4/2016 | Conway et al. |
| 2016/0106604 | A1 | 4/2016 | Timm |
| 2016/0113809 | A1 | 4/2016 | Kim |
| 2016/0135792 | A1 | 5/2016 | Cai |
| 2016/0136338 | A1 | 5/2016 | Lee et al. |
| 2016/0183689 | A1 | 6/2016 | Miner |
| 2016/0256022 | A1 | 9/2016 | Le |
| 2016/0270982 | A1 | 9/2016 | Raycheck et al. |
| 2016/0278662 | A1 | 9/2016 | Brister et al. |
| 2016/0327553 | A1 | 11/2016 | Edwards et al. |
| 2016/0357400 | A1 | 12/2016 | Penha et al. |
| 2016/0366699 | A1 | 12/2016 | Zhang et al. |
| 2016/0367226 | A1 | 12/2016 | Newton et al. |
| 2016/0367411 | A1 | 12/2016 | Justiz et al. |
| 2016/0367726 | A1 | 12/2016 | Gratzer |
| 2016/0374848 | A1* | 12/2016 | Sanchez .................. A61F 5/453 604/319 |
| 2017/0007438 | A1 | 1/2017 | Harvie |
| 2017/0014560 | A1 | 1/2017 | Minskoff et al. |
| 2017/0042724 | A1 | 2/2017 | Ugarte |
| 2017/0042748 | A1 | 2/2017 | Griffin |
| 2017/0049605 | A1 | 2/2017 | Wisniewski |
| 2017/0100276 | A1 | 4/2017 | Joh |
| 2017/0107312 | A1 | 4/2017 | Hinayama et al. |
| 2017/0128638 | A1 | 5/2017 | Giezendanner et al. |
| 2017/0136209 | A1 | 5/2017 | Burnett et al. |
| 2017/0143534 | A1 | 5/2017 | Sanchez |
| 2017/0165100 | A1 | 6/2017 | Jackson et al. |
| 2017/0165405 | A1 | 6/2017 | Muser et al. |
| 2017/0189225 | A1 | 7/2017 | Voorhees et al. |
| 2017/0202692 | A1 | 7/2017 | Laniado |
| 2017/0216081 | A1 | 8/2017 | Accosta |
| 2017/0238911 | A1 | 8/2017 | Duval |
| 2017/0246026 | A1 | 8/2017 | Laniado |
| 2017/0252014 | A1 | 9/2017 | Siller Gonzalez et al. |
| 2017/0252202 | A9 | 9/2017 | Sanchez et al. |
| 2017/0266031 | A1 | 9/2017 | Sanchez et al. |
| 2017/0266658 | A1 | 9/2017 | Bruno et al. |
| 2017/0281399 | A1 | 10/2017 | Vanmiddendorp et al. |
| 2017/0281419 | A1 | 10/2017 | Pintado |
| 2017/0312116 | A1 | 11/2017 | Laniado |
| 2017/0325788 | A1 | 11/2017 | Ealovega et al. |
| 2017/0333244 | A1 | 11/2017 | Laniado |
| 2017/0340489 | A1 | 11/2017 | Yamada |
| 2017/0348139 | A1 | 12/2017 | Newton et al. |
| 2017/0354532 | A1 | 12/2017 | Holt |
| 2017/0354551 | A1 | 12/2017 | Gawley et al. |
| 2017/0367873 | A1 | 12/2017 | Grannum |
| 2018/0002075 | A1 | 1/2018 | Lee |
| 2018/0008451 | A1 | 1/2018 | Stroebech |
| 2018/0008804 | A1 | 1/2018 | Laniado |
| 2018/0021218 | A1 | 1/2018 | Brosch et al. |
| 2018/0028349 | A1 | 2/2018 | Newton et al. |
| 2018/0037384 | A1 | 2/2018 | Archeny et al. |
| 2018/0049910 | A1 | 2/2018 | Newton |
| 2018/0064572 | A1 | 3/2018 | Wiltshire |
| 2018/0104131 | A1 | 4/2018 | Killian |
| 2018/0127187 | A1 | 5/2018 | Sewell |
| 2018/0149635 | A1 | 5/2018 | Abir |
| 2018/0169281 | A1 | 6/2018 | Russell et al. |
| 2018/0193215 | A1 | 7/2018 | Davies et al. |
| 2018/0200101 | A1 | 7/2018 | Su |
| 2018/0214297 | A1 | 8/2018 | Hughett et al. |
| 2018/0215649 | A1 | 8/2018 | Wada et al. |
| 2018/0221216 | A1 | 8/2018 | Benz et al. |
| 2018/0228642 | A1 | 8/2018 | Davis et al. |
| 2018/0229014 | A1 | 8/2018 | Guirguis et al. |
| 2018/0256384 | A1 | 9/2018 | Kasirye |
| 2018/0271694 | A1 | 9/2018 | Fernandez et al. |
| 2018/0280236 | A1 | 10/2018 | Ludin et al. |
| 2018/0317892 | A1 | 11/2018 | Catlin |
| 2018/0325748 | A1 | 11/2018 | Sharma et al. |
| 2019/0001029 | A1 | 1/2019 | Davie et al. |
| 2019/0001030 | A1 | 1/2019 | Braga et al. |
| 2019/0021899 | A1 | 1/2019 | Met |
| 2019/0029869 | A1 | 1/2019 | Huchthausen |
| 2019/0038451 | A1 | 2/2019 | Harvie |
| 2019/0046102 | A1 | 2/2019 | Kushnir et al. |
| 2019/0059938 | A1 | 2/2019 | Holsten |
| 2019/0060138 | A1 | 2/2019 | Marquez et al. |
| 2019/0091059 | A1 | 3/2019 | Gabriel |
| 2019/0100362 | A1 | 4/2019 | Meyers et al. |
| 2019/0133126 | A1 | 5/2019 | Modak et al. |
| 2019/0133814 | A1 | 5/2019 | Tammen et al. |
| 2019/0142624 | A1 | 5/2019 | Sanchez et al. |
| 2019/0224036 | A1 | 7/2019 | Sanchez et al. |

(56) References Cited

U.S. PATENT DOCUMENTS

| | | | | |
|---|---|---|---|---|
| 2019/0226189 | A1 | 7/2019 | Braxton | |
| 2019/0240079 | A1 | 8/2019 | Tuli | |
| 2019/0247222 | A1* | 8/2019 | Ecklund | A61F 5/443 |
| 2019/0247223 | A1 | 8/2019 | Brun et al. | |
| 2019/0247623 | A1 | 8/2019 | Helm et al. | |
| 2019/0282391 | A1* | 9/2019 | Johannes | A61F 13/15 |
| 2019/0314189 | A1 | 10/2019 | Acosta | |
| 2019/0314190 | A1 | 10/2019 | Sanchez et al. | |
| 2019/0321587 | A1 | 10/2019 | Mcmenamin et al. | |
| 2019/0344934 | A1 | 11/2019 | Faerber et al. | |
| 2019/0365303 | A1 | 12/2019 | Bullington et al. | |
| 2019/0365307 | A1 | 12/2019 | Laing et al. | |
| 2019/0365561 | A1 | 12/2019 | Newton et al. | |
| 2019/0374373 | A1 | 12/2019 | Joh | |
| 2020/0008985 | A1 | 1/2020 | Nguyen et al. | |
| 2020/0016012 | A1 | 1/2020 | Dutkiewicz | |
| 2020/0030595 | A1 | 1/2020 | Boukidjian et al. | |
| 2020/0040561 | A1 | 2/2020 | Sugawara | |
| 2020/0046544 | A1 | 2/2020 | Godinez et al. | |
| 2020/0055638 | A1 | 2/2020 | Lau et al. | |
| 2020/0070392 | A1 | 3/2020 | Huber et al. | |
| 2020/0085609 | A1 | 3/2020 | Schelch et al. | |
| 2020/0085610 | A1 | 3/2020 | Cohn et al. | |
| 2020/0086090 | A1 | 3/2020 | Von Weymarn-Schärli et al. | |
| 2020/0107518 | A1 | 4/2020 | Hiroshima et al. | |
| 2020/0129322 | A1 | 4/2020 | Leuckel | |
| 2020/0171217 | A9 | 6/2020 | Braga et al. | |
| 2020/0179177 | A1 | 6/2020 | Erdem et al. | |
| 2020/0187918 | A1 | 6/2020 | Wiygul | |
| 2020/0206015 | A1 | 7/2020 | Langer | |
| 2020/0206039 | A1 | 7/2020 | Mclain | |
| 2020/0214910 | A1 | 7/2020 | Varona et al. | |
| 2020/0216898 | A1 | 7/2020 | Hubbell | |
| 2020/0216989 | A1 | 7/2020 | Kinugasa et al. | |
| 2020/0229964 | A1 | 7/2020 | Staali et al. | |
| 2020/0231343 | A1 | 7/2020 | Freedman et al. | |
| 2020/0232841 | A1 | 7/2020 | Satish et al. | |
| 2020/0246172 | A1 | 8/2020 | Ho | |
| 2020/0246203 | A1 | 8/2020 | Tulk et al. | |
| 2020/0255189 | A1 | 8/2020 | Liu | |
| 2020/0261280 | A1* | 8/2020 | Heyman | A61F 13/471 |
| 2020/0276046 | A1 | 9/2020 | Staali et al. | |
| 2020/0306075 | A1 | 10/2020 | Newton et al. | |
| 2020/0315837 | A1 | 10/2020 | Radl et al. | |
| 2020/0315838 | A1 | 10/2020 | Eckert | |
| 2020/0315872 | A1 | 10/2020 | Viens et al. | |
| 2020/0315874 | A1 | 10/2020 | Viens et al. | |
| 2020/0331672 | A1 | 10/2020 | Bertram et al. | |
| 2020/0345332 | A1 | 11/2020 | Duval | |
| 2020/0352774 | A1 | 11/2020 | Rabinowitz et al. | |
| 2020/0353135 | A1 | 11/2020 | Gregory et al. | |
| 2020/0367677 | A1 | 11/2020 | Silsby et al. | |
| 2020/0369444 | A1 | 11/2020 | Silsby et al. | |
| 2020/0375781 | A1 | 12/2020 | Staali et al. | |
| 2020/0375810 | A1 | 12/2020 | Carlin et al. | |
| 2020/0384242 | A1 | 12/2020 | Havard et al. | |
| 2020/0385179 | A1 | 12/2020 | Mccourt | |
| 2020/0390591 | A1 | 12/2020 | Glithero et al. | |
| 2020/0390592 | A1 | 12/2020 | Merrill | |
| 2020/0398024 | A1 | 12/2020 | Fletter et al. | |
| 2020/0405521 | A1 | 12/2020 | Glasroe | |
| 2020/0405523 | A1 | 12/2020 | Obst et al. | |
| 2021/0007910 | A1 | 1/2021 | Furukawa | |
| 2021/0008771 | A1 | 1/2021 | Huber et al. | |
| 2021/0009323 | A1 | 1/2021 | Markarian et al. | |
| 2021/0020072 | A1 | 1/2021 | Moehring et al. | |
| 2021/0023279 | A1 | 1/2021 | Radl et al. | |
| 2021/0059853 | A1 | 3/2021 | Davis et al. | |
| 2021/0061523 | A1 | 3/2021 | Bytheway | |
| 2021/0069005 | A1 | 3/2021 | Sanchez et al. | |
| 2021/0069008 | A1 | 3/2021 | Blabas et al. | |
| 2021/0069009 | A1 | 3/2021 | Im | |
| 2021/0069030 | A1 | 3/2021 | Nishikawa et al. | |
| 2021/0077993 | A1 | 3/2021 | Nazareth et al. | |
| 2021/0113749 | A1 | 4/2021 | Radl et al. | |
| 2021/0121318 | A1 | 4/2021 | Pinlac | |
| 2021/0137724 | A1 | 5/2021 | Ecklund et al. | |
| 2021/0138190 | A1 | 5/2021 | Erbey et al. | |
| 2021/0154055 | A1 | 5/2021 | Villarreal | |
| 2021/0170079 | A1 | 6/2021 | Radl et al. | |
| 2021/0178390 | A1 | 6/2021 | Oueslati et al. | |
| 2021/0186742 | A1 | 6/2021 | Newton et al. | |
| 2021/0186744 | A1 | 6/2021 | Spector | |
| 2021/0206144 | A1 | 7/2021 | Ewell | |
| 2021/0211568 | A1 | 7/2021 | Zhou et al. | |
| 2021/0212865 | A1 | 7/2021 | Wallajapet et al. | |
| 2021/0220162 | A1 | 7/2021 | Jamison | |
| 2021/0220163 | A1 | 7/2021 | Mayrand | |
| 2021/0228400 | A1 | 7/2021 | Glithero | |
| 2021/0228401 | A1 | 7/2021 | Becker et al. | |
| 2021/0228795 | A1 | 7/2021 | Hughett et al. | |
| 2021/0229877 | A1 | 7/2021 | Ragias et al. | |
| 2021/0236323 | A1 | 8/2021 | Austermann et al. | |
| 2021/0236324 | A1 | 8/2021 | Sweeney | |
| 2021/0251814 | A1 | 8/2021 | Jönegren et al. | |
| 2021/0267787 | A1 | 9/2021 | Nazemi | |
| 2021/0275343 | A1 | 9/2021 | Sanchez et al. | |
| 2021/0275344 | A1 | 9/2021 | Wing | |
| 2021/0290454 | A1 | 9/2021 | Yamada | |
| 2021/0290464 | A1 | 9/2021 | Furuta | |
| 2021/0315726 | A1 | 10/2021 | Lin | |
| 2021/0315727 | A1 | 10/2021 | Jiang | |
| 2021/0353449 | A1 | 11/2021 | Sharma et al. | |
| 2021/0353450 | A1 | 11/2021 | Sharma et al. | |
| 2021/0361469 | A1 | 11/2021 | Liu et al. | |
| 2021/0369495 | A1 | 12/2021 | Cheng et al. | |
| 2021/0386925 | A1 | 12/2021 | Hartwell et al. | |
| 2021/0393433 | A1 | 12/2021 | Godinez et al. | |
| 2022/0015958 | A1 | 1/2022 | Ito | |
| 2022/0023091 | A1 | 1/2022 | Ecklund et al. | |
| 2022/0026546 | A1 | 1/2022 | Aono et al. | |
| 2022/0031290 | A1 | 2/2022 | Weed | |
| 2022/0031523 | A1 | 2/2022 | Pierpoint | |
| 2022/0039995 | A1 | 2/2022 | Johannes et al. | |
| 2022/0047410 | A1 | 2/2022 | Walthall | |
| 2022/0062025 | A1 | 3/2022 | Shields et al. | |
| 2022/0062027 | A1 | 3/2022 | Mitchell et al. | |
| 2022/0062028 | A1 | 3/2022 | Mitchell et al. | |
| 2022/0062029 | A1 | 3/2022 | Johannes et al. | |
| 2022/0066825 | A1 | 3/2022 | Saraf et al. | |
| 2022/0071811 | A1 | 3/2022 | Cheng et al. | |
| 2022/0071826 | A1 | 3/2022 | Kulkarni et al. | |
| 2022/0104965 | A1 | 4/2022 | Vaninetti et al. | |
| 2022/0104976 | A1 | 4/2022 | Hoeger et al. | |
| 2022/0104981 | A1 | 4/2022 | Jones | |
| 2022/0117773 | A1 | 4/2022 | Davis et al. | |
| 2022/0117774 | A1 | 4/2022 | Meyer et al. | |
| 2022/0117775 | A1 | 4/2022 | Jones et al. | |
| 2022/0118165 | A1 | 4/2022 | Knapp et al. | |
| 2022/0133524 | A1 | 5/2022 | Davis | |
| 2022/0151817 | A1 | 5/2022 | Mann | |
| 2022/0160949 | A1 | 5/2022 | Simiele et al. | |
| 2022/0168159 | A1 | 6/2022 | Triado et al. | |
| 2022/0193312 | A1 | 6/2022 | Lee et al. | |
| 2022/0211536 | A1 | 7/2022 | Johannes et al. | |
| 2022/0218510 | A1 | 7/2022 | Metzger et al. | |
| 2022/0229053 | A1 | 7/2022 | Levin et al. | |
| 2022/0241106 | A1 | 8/2022 | Johannes et al. | |
| 2022/0247407 | A1 | 8/2022 | Yamamoto et al. | |
| 2022/0248836 | A1 | 8/2022 | Cagle et al. | |
| 2022/0257407 | A1 | 8/2022 | Johannes et al. | |
| 2022/0265460 | A1 | 8/2022 | Coker | |
| 2022/0265462 | A1 | 8/2022 | Alder et al. | |
| 2022/0270711 | A1 | 8/2022 | Feala et al. | |
| 2022/0273482 | A1 | 9/2022 | Johannes et al. | |
| 2022/0280357 | A1 | 9/2022 | Jagannathan et al. | |
| 2022/0280710 | A1 | 9/2022 | Agrawal et al. | |
| 2022/0287689 | A1 | 9/2022 | Johannes | |
| 2022/0287691 | A1 | 9/2022 | Wormser et al. | |
| 2022/0287867 | A1 | 9/2022 | Jones et al. | |
| 2022/0287868 | A1 | 9/2022 | Garvey et al. | |
| 2022/0296408 | A1 | 9/2022 | Evans et al. | |
| 2022/0305191 | A1 | 9/2022 | Joseph et al. | |
| 2022/0313222 | A1 | 10/2022 | Austermann et al. | |

(56) References Cited

U.S. PATENT DOCUMENTS

| | | | |
|---|---|---|---|
| 2022/0313474 | A1 | 10/2022 | Kriscovich et al. |
| 2022/0331170 | A1 | 10/2022 | Erdem et al. |
| 2022/0339023 | A1 | 10/2022 | Davis et al. |
| 2022/0339024 | A1 | 10/2022 | Johannes et al. |
| 2022/0354685 | A1 | 11/2022 | Davis et al. |
| 2022/0362049 | A1 | 11/2022 | Austermann et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |
| 2022/0387001 | A1 | 12/2022 | Askenazi et al. |
| 2022/0387693 | A1 | 12/2022 | Bannwart et al. |
| 2022/0395390 | A1 | 12/2022 | Brooks |
| 2022/0395391 | A1 | 12/2022 | Saunders et al. |
| 2022/0401252 | A1 | 12/2022 | Warren |
| 2022/0409419 | A1 | 12/2022 | Garvey et al. |
| 2022/0409422 | A1 | 12/2022 | Schneider et al. |
| 2023/0018845 | A1 | 1/2023 | Lee |
| 2023/0020563 | A1 | 1/2023 | Sharma et al. |
| 2023/0031640 | A1 | 2/2023 | Hughett et al. |
| 2023/0037159 | A1 | 2/2023 | Brennan et al. |
| 2023/0049924 | A1 | 2/2023 | Johannes et al. |
| 2023/0052238 | A1 | 2/2023 | Oluwasogo |
| 2023/0062944 | A1 | 3/2023 | Vollenberg et al. |
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0091118 | A1 | 3/2023 | Watson |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Mn et al. |
| 2023/0190511 | A1 | 6/2023 | Sharma et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277360 | A1 | 9/2023 | Lambert et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0389900 | A1 | 12/2023 | Xie et al. |
| 2023/0404791 | A1 | 12/2023 | Ecklund et al. |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0341998 | A1 | 10/2024 | Julian et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |
| 2025/0367358 | A1 | 12/2025 | Smith et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |
| CA | 2359091 | C | 9/2003 |
| CA | 1533755 | A | 10/2004 |
| CA | 2488867 | C | 8/2007 |
| CA | 103717180 | A | 4/2014 |
| CA | 3031934 | A1 | 2/2018 |
| CA | 107847384 | A | 3/2018 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |
| CN | 1332620 | A | 1/2002 |
| CN | 1434693 | A | 8/2003 |
| CN | 1579348 | A | 2/2005 |
| CN | 1602825 | A | 4/2005 |
| CN | 1638708 | A | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 204562697 | U | 8/2015 |
| CN | 105411783 | A | 3/2016 |
| CN | 105451607 | A | 3/2016 |
| CN | 105451693 | A | 3/2016 |
| CN | 105534632 | A | 5/2016 |
| CN | 106132360 | A | 11/2016 |
| CN | 106137631 | A | 11/2016 |
| CN | 205849719 | U | 1/2017 |
| CN | 205924282 | U | 2/2017 |
| CN | 106726089 | A | 5/2017 |
| CN | 107920912 | A | 4/2018 |
| CN | 108420590 | A | 8/2018 |
| CN | 207785556 | U | 8/2018 |
| CN | 110171118 | A | 8/2019 |
| CN | 209285902 | U | 8/2019 |
| CN | 110381883 | A | 10/2019 |
| CN | 111465375 | A | 7/2020 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |

(56) References Cited

FOREIGN PATENT DOCUMENTS

| | | | |
|---|---|---|---|
| DE | 1516466 | A1 | 6/1969 |
| DE | 2721330 | A1 | 11/1977 |
| DE | 2742298 | A1 | 3/1978 |
| DE | 3104356 | A1 | 9/1982 |
| DE | 9407554.9 | U1 | 5/1995 |
| DE | 9407554 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | U1 | 6/2006 |
| DE | 102005037762 | B3 | 9/2006 |
| DE | 202006018506 | U1 | 3/2007 |
| DE | 102011103783 | A1 | 12/2012 |
| DE | 102012112818 | A1 | 6/2014 |
| DE | 202015104597 | U1 | 7/2016 |
| DE | 102018118570 | A1 | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0945231 | A2 | 9/1999 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| FR | 2294812 | A1 | 7/1976 |
| FR | 2826704 | A1 | 1/2003 |
| GB | 871820 | A | 7/1961 |
| GB | 873045 | A | 7/1961 |
| GB | 996370 | A | 6/1965 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| GE | 2191095 | A | 12/1987 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |

(56) References Cited

FOREIGN PATENT DOCUMENTS

| | | | |
|---|---|---|---|
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 5/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 101035745 | B1 | 5/2011 |
| KR | 20120005922 | A | 1/2012 |
| KR | 20140039485 | A | 4/2014 |
| KR | 101432639 | B1 | 8/2014 |
| KR | 20180022173 | A | 3/2018 |
| KR | 20180106659 | A | 10/2018 |
| KR | 20180108774 | A | 10/2018 |
| KR | 101976679 | B1 | 5/2019 |
| KR | 101998130 | B1 | 7/2019 |
| KR | 20230034343 | A | 3/2023 |
| PT | 2068717 | E | 6/2013 |
| SE | 505542 | C2 | 9/1997 |
| TW | 408207 | B | 10/2000 |
| TW | 202123903 | A | 7/2021 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005003725 | A2 | 1/2005 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |

(56) References Cited

FOREIGN PATENT DOCUMENTS

| | | | |
|---|---|---|---|
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018200721 | A1 | 11/2018 |
| WO | 2018235026 | A1 | 12/2018 |
| WO | 2018235065 | A1 | 12/2018 |
| WO | 2019004404 | A1 | 1/2019 |
| WO | 2019038732 | A1 | 2/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |

(56) References Cited

FOREIGN PATENT DOCUMENTS

| | | | |
|---|---|---|---|
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Application No. 15/260, 103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.

(56) References Cited

OTHER PUBLICATIONS

International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 2021.
International Search Report and Written Opinion from International Application No. PCT/US2021/027913 mailed Jul. 12, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021,.
Issue Notification for U.S. Appl. No. 29/624,661 mailed Aug. 4, 2021,.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/899,956 mailed Oct. 16, 2020.
Non-Final Office Action for U.S. Appl. No. 16/904,868 mailed Nov. 25, 2020.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 17/088,272 mailed Aug. 5, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.

(56) References Cited

OTHER PUBLICATIONS

U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/444,825, filed Aug. 10, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/073,545, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/214,551, filed Jun. 24, 2021.
U.S. Appl. No. 63/214,570, filed Jun. 24, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
Defendant and Counterclaim Plaintiff Sage Products, LLC's Answer, Defenses, and Counterclaims To Plaintiff's Amended Complaint, Nov. 1, 2019.
Memorandum Order, Feb. 2021, 14 pgs.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Boehringer CareDry System—Second Generation for Non-Invasive Urinary Management for Females, Mar. 2021, 3 pgs.
Excerpts from the 508 (Patent No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.

(56) References Cited

OTHER PUBLICATIONS

"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Advisory Action for U.S. Appl. No. 16/433,773 mailed Feb. 15, 2023.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 17/662,700 mailed Jan. 30, 2023.
Corrected Notice of Allowability for U.S. Appl. No. 17/330,657 mailed Dec. 9, 2021.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/904,868 mailed Mar. 10, 2022.
Final Office Action for U.S. Appl. No. 16/905,400 mailed Dec. 9, 2021.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2021/015024 mailed May 18, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027917 mailed Aug. 19, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.

(56) References Cited

OTHER PUBLICATIONS

International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/044107 mailed Dec. 23, 2022.
Issue Notification for U.S. Appl. No. 16,905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/899,956 mailed Sep. 2, 2021.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 17/051,550 mailed Dec. 15, 2022.
Non-Final Office Action for U.S. Appl. No. 17/330,657 mailed Aug. 11, 2021.
Non-Final Office Action for U.S. Appl. No. 17/444,792 mailed Feb. 10, 2023.
Non-Final Office Action for U.S. Appl. No. 17/448,811 mailed Mar. 1, 2023.
Non-Final Office Action for U.S. Appl. No. 17/451,345 mailed Dec. 7, 2022.
Non-Final Office Action for U.S. Appl. No. 17/662,700 mailed Jul. 22, 2022.
Non-Final Office Action for U.S. Appl. No. 29/741,751 mailed Jan. 18, 2022.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Feb. 22, 2023.
Notice of Allowance for U.S. Appl. No. 17/461,036 mailed Oct. 6, 2022.

(56) References Cited

OTHER PUBLICATIONS

Notice of Allowance for U.S. Appl. No. 17/663,046 mailed Jan. 30, 2023.
Notice of Allowance for U.S. Appl. No. 29/741,751 mailed Jun. 9, 2022.
Restriction Requirement for U.S. Appl. No. 16/433,773 mailed Dec. 7, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 16/245,726, filed Jan. 11, 2019.
U.S. Appl. No. 17/394,055, filed Aug. 4, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/164,800, filed Feb. 6, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/047,374, filed Jul. 2, 2020.
U.S. Appl. No. 63/073,553, filed Sep. 2, 2020.
U.S. Appl. No. 63/094,646, filed Oct. 21, 2020.
U.S. Appl. No. 63/109,084, filed Nov. 3, 2020.
U.S. Appl. No. 63/133,892, filed Jan. 5, 2021.
U.S. Appl. No. 63/138,878, filed Jan. 19, 2021.
U.S. Appl. No. 63/159,186, filed Mar. 10, 2021.
U.S. Appl. No. 63/191,558, filed May 21, 2021.
U.S. Appl. No. 63/192,289, filed May 24, 2021.
U.S. Appl. No. 63/193,891, filed May 27, 2021.
U.S. Appl. No. 63/208,262, filed Jun. 8, 2021.
U.S. Appl. No. 63/215,017, filed Jun. 25, 2021.
U.S. Appl. No. 63/228,244, filed Aug. 2, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Parness , et al., "A microfabricated wedge-shaped adhesive array displaying gecko-like dynamic adhesion, directionality", J.R. Soc. Interface, 2009, pp. 1223-1232.

(56) References Cited

OTHER PUBLICATIONS

Tsipenyuk , et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Final Office Action for U.S. Appl. No. 16/478,180 mailed May 31, 2023.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/444,792 mailed Jun. 15, 2023.
Final Office Action for U.S. Appl. No. 17/451,345 mailed May 3, 2023.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
Issue Notification for U.S. Appl. No. 16/899,956 mailed Mar. 29, 2023.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 16/904,868 mailed Mar. 15, 2023.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/450,864 mailed May 10, 2023.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Notice of Allowance for U.S. Appl. No. 16/245,726 mailed Jul. 6, 2023.
Notice of Allowance for U.S. Appl. No. 17/051,554 mailed Jul. 6, 2023.
Notice of Allowance for U.S. Appl. No. 17/461,036 mailed Jun. 30, 2023.
Notice of Allowance for U.S. Appl. No. 17/662,700 mailed Mar. 28, 2023.
Restriction Requirement for U.S. Appl. No. 17/326,980 mailed Mar. 20, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 17/664,487, filed May 23, 2022.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
*PureWick Corporation* v. *Sage Products, LLC Transcripts* vol. 5, Apr. 1, 2022, 72 pages.
*PureWick Corporation* v. *Sage Products, LLC Transcripts* vol. 1, Mar. 28, 2022, 99 pages.
*PureWick Corporation* v. *Sage Products, LLC Transcripts* vol. 2, Mar. 29, 2022, 106 pages.
*PureWick Corporation* v. *Sage Products, LLC Transcripts* vol. 3, Mar. 30, 2022, 115 pages.
*PureWick Corporation* v. *Sage Products, LLC Transcripts* vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Pieper , et al., "An external urine-collection device for women: A clinical trial", Journal of ER Nursing, vol. 20, No. 2, Mar./Apr. 1993, pp. 51-55.
Vinas , "A Solution For An Awkward—But Serious—Subject", http://www.aero-news.net/index.cfm?do=main.textpost&id=69ae2bb1-838b-4098-a7b5-7flbb2505688 last accessed Feb. 8, 2021, 3 pages.
Advisory Action for U.S. Appl. No. 16/478,180 mailed Sep. 7, 2023.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/444,792 mailed Aug. 25, 2023.
Advisory Action for U.S. Appl. No. 17/448,811 mailed Nov. 15, 2023.
Advisory Action for U.S. Appl. No. 17/451,345 mailed Oct. 20, 2023.

(56) References Cited

OTHER PUBLICATIONS

Advisory Action for U.S. Appl. No. 17/653,137 mailed Dec. 1, 2023.
Advisory Action for U.S. Appl. No. 17/655,464 mailed Dec. 13, 2023.
Corrected Notice of Allowance for U.S. Appl. No. 16/369,676 mailed Dec. 7, 2023.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/904,868 mailed Nov. 2, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/448,811 mailed Aug. 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 18/164,800 mailed Dec. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
Issue Notification for U.S. Appl. No. 16/245,726 mailed Oct. 18, 2023.
Issue Notification for U.S. Appl. No. 17/461,036 mailed Oct. 11, 2023.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/051,399 mailed Aug. 18, 2023.
Non-Final Office Action for U.S. Appl. No. 17/051,550 mailed Oct. 24, 2023.
Non-Final Office Action for U.S. Appl. No. 17/444,792 mailed Nov. 17, 2023.
Non-Final Office Action for U.S. Appl. No. 17/446,654 mailed Sep. 8, 2023.
Non-Final Office Action for U.S. Appl. No. 17/453,560 mailed Oct. 16, 2023.
Non-Final Office Action for U.S. Appl. No. 17/645,821 mailed Oct. 25, 2023.
Non-Final Office Action for U.S. Appl. No. 17/657,474 mailed Sep. 12, 2023.
Non-Final Office Action for U.S. Appl. No. 17/808,354 mailed Nov. 28, 2023.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/198,464 mailed Dec. 7, 2023.
Notice of Allowance for U.S. Appl. No. 16/369,676 mailed Nov. 14, 2023.
Notice of Allowance for U.S. Appl. No. 17/051,554 mailed Oct. 18, 2023.
Notice of Allowance for U.S. Appl. No. 17/662,700 mailed Jul. 28, 2023.
Notice of Allowance for U.S. Appl. No. 17/662,700 mailed Nov. 15, 2023.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/645,821 mailed Jul. 12, 2023.
Restriction Requirement for U.S. Appl. No. 18/134,857 mailed Oct. 23, 2023.
U.S. Appl. No. 17/451,719, filed Oct. 19, 2021.
U.S. Appl. No. 18/263,800, filed Aug. 1, 2023.
U.S. Appl. No. 18/264,004, filed Aug. 2, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 63/150,640, filed Feb. 18, 2021.
U.S. Appl. No. 63/596,012, filed Nov. 3, 2023.
U.S. Appl. No. 63/608,553, filed Dec. 11, 2023.
Merriam-Webster Dictionary, “Embed Definition & Meaning”, https://www.merriam-webster.com/dictionary/embed last accessed Aug. 3, 2023, 2003.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/904,868 mailed Jan. 2, 2024.
Advisory Action for U.S. Appl. No. 17/179,116 mailed Jan. 8, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/139,523 mailed Apr. 24, 2024.

(56) References Cited

OTHER PUBLICATIONS

Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 17/051,399 mailed Jan. 8, 2024.
Final Office Action for U.S. Appl. No. 17/444,792 mailed Apr. 3, 2024.
Final Office Action for U.S. Appl. No. 17/446,654 mailed Jan. 31, 2024.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/904,868 mailed Mar. 12, 2024.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/664,914 mailed Jan. 31, 2024.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/164,800 mailed Mar. 22, 2024.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/667,097 mailed Mar. 20, 2024.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/415,080, filed Jan. 17, 2024.
U.S. Appl. No. 18/426,795, filed Jan. 30, 2024.
U.S. Appl. No. 18/584,002, filed Feb. 22, 2024.
U.S. Appl. No. 18/610,523, filed Mar. 20, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/561,893, filed Dec. 11, 2023.

(56) References Cited

OTHER PUBLICATIONS

Wikipedia Article, "Decibel", https://web.archive.org/web/20200415211917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081 , version of Jun. 1, 2016, 7 pages.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/451,345 mailed Jul. 3, 2024.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/808,354 mailed Jun. 12, 2024.
Advisory Action for U.S. Appl. No. 18/134,857 mailed Oct. 23, 2024.
Advisory Action for U.S. Appl. No. 18/140,163 mailed Jun. 3, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Final Office Action for U.S. Appl. No. 16/433,773 mailed Sep. 9, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Application No. 17/447, 123 mailed May 14, 2024.
Final Office Action for U.S. Appl. No. 17/451,354 mailed Oct. 28, 2024.
Final Office Action for U.S. Appl. No. 17/597,673 mailed Oct. 22, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/030365 mailed Mar. 13, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 18/198,464 mailed Nov. 20, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/389,009 mailed May 24, 2024.

(56) References Cited

OTHER PUBLICATIONS

Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/452,145 mailed Jul. 11, 2024.
Notice of Allowance for U.S. Appl. No. 16/904,868 mailed Sep. 29, 2024.
Notice of Allowance for U.S. Appl. No. 17/179,116 mailed Sep. 13, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/426,795 mailed Nov. 20, 2024.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/878,268 mailed Sep. 20, 2024.
U.S. Appl. No. 17/013,822, filed Sep. 7, 2020.
U.S. Appl. No. 18/662,216, filed May 13, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"OBLONG", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Advisory Action for U.S. Appl. No. 17/446,654 mailed Feb. 28, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 18/003,029 mailed Jan. 8, 2025.
Advisory Action for U.S. Appl. No. 18/164,800 mailed Jan. 8, 2025.
Corrected Notice of Allowability for U.S. Appl. No. 17/646,771 mailed Jan. 17, 2025.
Corrected Notice of Allowability for U.S. Appl. No. 18/134,857 mailed Mar. 14, 2025.
Corrected Notice of Allowability for U.S. Appl. No. 18/426,795 mailed Dec. 4, 2024.
Final Office Action for U.S. Appl. No. 16/452,258 mailed Jan. 6, 2025.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/625,941 mailed Feb. 18, 2025.
Final Office Action for U.S. Appl. No. 17/653,314 mailed Jan. 30, 2025.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/757,311 mailed Mar. 31, 2025.
International Search Report and Written Opinion from International Application No. PCT/US2023/031432 mailed Feb. 29, 2024.
International Search Report and Written Opinion from International Application No. PCT/US2024/053681 mailed Jan. 27, 2025.
Issue Notification for U.S. Appl. No. 16/478,180 mailed Mar. 5, 2025.
Issue Notification for U.S. Appl. No. 17/051,585 mailed Mar. 26, 2025.

(56) References Cited

OTHER PUBLICATIONS

Issue Notification for U.S. Appl. No. 17/179,116 mailed Dec. 25, 2024.
Issue Notification for U.S. Appl. No. 17/450,864 mailed Jan. 8, 2025.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/646,771 mailed Mar. 19, 2025.
Issue Notification for U.S. Appl. No. 17/661,090 mailed Feb. 5, 2025.
Issue Notification for U.S. Appl. No. 17/663,330 mailed Feb. 26, 2025.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/389,009 mailed Dec. 18, 2024.
Issue Notification for U.S. Appl. No. 18/426,795 mailed Feb. 19, 2025.
Non-Final Office Action for U.S. Appl. No. 16/433,773 mailed Feb. 28, 2025.
Non-Final Office Action for U.S. Appl. No. 17/051,600 mailed Feb. 28, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/451,354 mailed Mar. 19, 2025.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Application No. 17/653, 137 mailed Jan. 28, 2025.
Non-Final Office Action for U.S. Appl. No. 17/655,464 mailed Mar. 20, 2025.
Non-Final Office Action for U.S. Appl. No. 17/754,736 mailed Mar. 31, 2025.
Non-Final Office Action for U.S. Appl. No. 17/758,152 mailed Apr. 8, 2025.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/907,125 mailed Dec. 13, 2024.
Non-Final Office Action for U.S. Appl. No. 17/996,064 mailed Mar. 6, 2025.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 17/051,585 mailed Dec. 26, 2024.
Notice of Allowance for U.S. Appl. No. 17/444,792 mailed Mar. 28, 2025.
Notice of Allowance for U.S. Appl. No. 17/596,629 mailed Jan. 29, 2025.
Notice of Allowance for U.S. Appl. No. 17/597,673 mailed Feb. 26, 2025.
Notice of Allowance for U.S. Appl. No. 17/646,771 mailed Dec. 17, 2024.
Notice of Allowance for U.S. Appl. No. 17/749,340 mailed Feb. 14, 2025.
Notice of Allowance for U.S. Appl. No. 17/758,316 mailed Mar. 24, 2025.
Notice of Allowance for U.S. Application No. 17/996, 155 mailed Mar. 11, 2025.
Notice of Allowance for U.S. Appl. No. 18/134,857 mailed Feb. 20, 2025.
Notice of Allowance for U.S. Appl. No. 18/415,080 mailed Dec. 30, 2024.
Notice of Allowance for U.S. Appl. No. 18/584,002 mailed Jan. 8, 2025.
Restriction Requirement for U.S. Appl. No. 17/809,083 mailed Dec. 31, 2024.
Restriction Requirement for U.S. Appl. No. 17/929,887 mailed Mar. 10, 2025.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/171,983, filed Apr. 7, 2025.
U.S. Appl. No. 63/181,709, filed Apr. 29, 2021.
U.S. Appl. No. 63/564,696, filed Mar. 13, 2024.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
"Surface Energy Data for Cellulose acetate, CAS # 9004-35-7", Diviersified Enterprises, 2009, 1 page.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/450,864 mailed on Mar. 21, 2024.
Advisory Action for U.S. Appl. No. 17/451,345 mailed May 13, 2025.
Advisory Action for U.S. Appl. No. 17/664,487 mailed Apr. 24, 2025.
Advisory Action for U.S. Appl. No. 17/757,311 mailed Jul. 2, 2025.
Corrected Notice of Allowability for U.S. Appl. No. 17/444,792 mailed Jun. 24, 2025.
Corrected Notice of Allowability for U.S. Appl. No. 17/996,253 mailed Apr. 28, 2025.
Corrected Notice of Allowability for U.S. Appl. No. 18/260,122 mailed Aug. 11, 2025.
Corrected Notice of Allowance for U.S. Appl. No. 17/444,792 mailed Jun. 24, 2025.
Corrected Notice of Allowance for U.S. Appl. No. 17/653,314 mailed Oct. 29, 2025.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 17/051,600 mailed Aug. 6, 2025.

(56) References Cited

OTHER PUBLICATIONS

Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/614,173 mailed May 20, 2025.
Final Office Action for U.S. Appl. No. 17/628,411 mailed Apr. 30, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,920 mailed Apr. 24, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/139,523 mailed May 8, 2025.
U.S. Appl. No. 19/370,361, filed Oct. 27, 2025.
Search Report and Written Opinion from International Application No. PCT/US2024/058598 mailed Mar. 28, 2025.
Search Report and Written Opinion from International Application No. PCT/US2025/018907 mailed May 16, 2025.
Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/904,868 mailed Apr. 30, 2025.
Issue Notification for U.S. Appl. No. 17/444,792 mailed Jun. 25, 2025.
Issue Notification for U.S. Appl. No. 17/597,673 mailed Jun. 4, 2025.
Issue Notification for U.S. Appl. No. 17/653,920 mailed Oct. 22, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 18/134,857 mailed May 28, 2025.
Issue Notification for U.S. Appl. No. 18/415,080 mailed Apr. 9, 2025.
Issue Notification for U.S. Appl. No. 18/584,002 mailed Apr. 16, 2025.
Non-Final Office Action for U.S. Appl. No. 16/452,258 mailed Sep. 24, 2025.
Non-Final Office Action for U.S. Appl. No. 17/446,654 mailed May 1, 2025.
Non-Final Office Action for U.S. Appl. No. 17/595,747 mailed Jun. 12, 2025.
Non-Final Office Action for U.S. Appl. No. 17/635,866 mailed Jul. 29, 2025.
Non-Final Office Action for U.S. Appl. No. 17/653,314 mailed May 8, 2025.
Non-Final Office Action for U.S. Appl. No. 17/664,487 mailed May 19, 2025.
Non-Final Office Action for U.S. Appl. No. 17/756,201 mailed Apr. 24, 2025.
Non-Final Office Action for U.S. Appl. No. 17/759,697 mailed Sep. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/115,444 mailed Oct. 22, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/247,986 mailed Jun. 4, 2025.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/548,152 mailed Sep. 16, 2025.
Non-Final Office Action for U.S. Appl. No. 18/553,625 mailed Oct. 2, 2025.
Non-Final Office Action for U.S. Appl. No. 18/757,964 mailed Aug. 20, 2025.
Notice of Allowance for U.S. Appl. No. 16/433,773 mailed Oct. 10, 2025.
Notice of Allowance for U.S. Appl. No. 17/451,345 mailed Jun. 24, 2025.
Notice of Allowance for U.S. Appl. No. 17/596,629 mailed May 27, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/755,236 mailed Jul. 17, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.

(56) References Cited

OTHER PUBLICATIONS

Notice of Allowance for U.S. Appl. No. 18/044,413 mailed Sep. 16, 2025.
Notice of Allowance for U.S. Appl. No. 18/260,122 mailed Jul. 30, 2025.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/551,492 mailed Nov. 10, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 19/127,234, filed May 5, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/356,506, filed Oct. 13, 2025.
U.S. Appl. No. 19/358,647, filed Oct. 15, 2025.
"PROXIMATE Definition & Meaning" <https://www.merriam-webster.com/dictionary/> 2025.
"Tube Definition & Meaning" Merriam Webster Dictionary, 2025, <https://www.merriam-webster.com/dictionary/tube>.
Advisory Action for U.S. Appl. No. 17/394,055 mailed Jan. 9, 2026.
Advisory Action for U.S. Appl. No. 18/265,736 mailed Mar. 4, 2026.
Corrected Notice of Allowability for U.S. Appl. No. 17/754,736 mailed Feb. 12, 2026.
Corrected Notice of Allowability for U.S. Appl. No. 17/808,354 mailed Nov. 25, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Final Office Action for U.S. Appl. No. 16/452,258 mailed Feb. 11, 2026.
Final Office Action for U.S. Appl. No. 17/446,654 mailed Dec. 22, 2025.
Final Office Action for U.S. Appl. No. 17/595,747 mailed Feb. 19, 2026.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/809,083 mailed Jan. 23, 2026.
Final Office Action for U.S. Appl. No. 17/929,887, filed Jan. 13, 2026.
Final Office Action for U.S. Appl. No. 17/933,590 mailed Feb. 19, 2026.
Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/164,800 mailed Dec. 5, 2025.
Final Office Action for U.S. Appl. No. 18/247,986 mailed Jan. 7, 2026.
Final Office Action for U.S. Appl. No. 18/265,736 mailed Dec. 1, 2025.
Search Report and Written Opinion from International Application No. PCT/US2023/036875 mailed May 31, 2024.
Search Report and Written Opinion from International Application No. PCT/US2023/077205 mailed Jul. 19, 2024.
Issue Notification for U.S. Appl. No. 16/433,773 mailed Jan. 21, 2026.
Issue Notification for U.S. Appl. No. 17/051,399 mailed Mar. 4, 2026.
Issue Notification for U.S. Appl. No. 17/451,354 mailed Feb. 25, 2026.
Issue Notification for U.S. Appl. No. 17/625,941 mailed Feb. 25, 2026.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/260,122 mailed Nov. 12, 2025.
Non-Final Office Action for U.S. Appl. No. 17/378,015 mailed Dec. 12, 2025.
Non-Final Office Action for U.S. Appl. No. 17/614,173 mailed Dec. 29, 2025.
Non-Final Office Action for U.S. Appl. No. 17/628,411 mailed Dec. 22, 2025.
Non-Final Office Action for U.S. Appl. No. 17/757,311 mailed Sep. 2, 2025.
Non-Final Office Action for U.S. Appl. No. 17/759,587 mailed Jan. 26, 2026.
Non-Final Office Action for U.S. Appl. No. 17/996,556 mailed Dec. 22, 2025.
Non-Final Office Action for U.S. Appl. No. 18/034,902 mailed Mar. 20, 2026.
Non-Final Office Action for U.S. Appl. No. 18/043,807 mailed Feb. 10, 2026.
Non-Final Office Action for U.S. Appl. No. 18/139,523 mailed Nov. 19, 2025.
Non-Final Office Action for U.S. Appl. No. 18/246,121 mailed Jan. 22, 2026.
Non-Final Office Action for U.S. Appl. No. 18/249,577 mailed Nov. 17, 2025.

(56) References Cited

OTHER PUBLICATIONS

Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,394, filed Jan. 13, 2026.
Non-Final Office Action for U.S. Appl. No. 18/263,800 mailed Feb. 5, 2026.
Non-Final Office Action for U.S. Appl. No. 18/376,274 mailed Mar. 9, 2026.
Non-Final Office Action for U.S. Appl. No. 18/549,387 mailed Mar. 4, 2026.
Non-Final Office Action for U.S. Appl. No. 18/551,492 mailed Mar. 19, 2026.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/662,216 mailed Mar. 9, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Mar. 27, 2026.
Non-Final Office Action for U.S. Appl. No. 29/892,478 mailed Mar. 12, 2026.
Notice of Allowance for U.S. Appl. No. 17/051,399 mailed Nov. 17, 2025.
Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/451,354 mailed Nov. 18, 2025.
Notice of Allowance for U.S. Appl. No. 17/625,887 mailed Mar. 3, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/754,736 mailed Jan. 28, 2026.
Notice of Allowance for U.S. Appl. No. 17/759,697 mailed Jan. 30, 2026.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 18/041,109 mailed Mar. 25, 2026.
Notice of Allowance for U.S. Appl. No. 18/264,004 mailed Jan. 30, 2026.
Notice of Allowance for U.S. Appl. No. 18/294,370 mailed Mar. 17, 2026.
Notice of Allowance for U.S. Appl. No. 18/610,523 mailed Mar. 4, 2026.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 18/687,117 mailed Mar. 26, 2026.
Restriction Requirement for U.S. Appl. No. 19/237,638 mailed Dec. 18, 2025.
U.S. Appl. No. 17/051,399, filed Oct. 28, 2020.
U.S. Appl. No. 17/625,941, filed Jan. 10, 2022.
U.S. Appl. No. 18/034,902, filed May 2, 2023.
U.S. Appl. No. 19/329,723, filed Sep. 16, 2025.
U.S. Appl. No. 19/337,217, filed Sep. 23, 2025.
U.S. Appl. No. 19/353,151, filed Oct. 8, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100, filed Feb. 25, 2026.
U.S. Appl. No. 19/534,156, filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125, filed Mar. 2, 2026.

* cited by examiner

SYSTEMS AND METHODS INCLUDING A MALE FLUID COLLECTION DEVICE AND A SECUREMENT ELEMENT

CROSS-REFERENCE TO RELATED APPLICATIONS

This application claims priority to U.S. Provisional Patent Application No. 63/073,545 filed on Sep. 2, 2020, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, pressure ulcers spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are directed to male fluid collection devices and methods of collecting fluid from a male. In an embodiment, a male fluid collection device includes a body defining a chamber sized to receive at least a head of a penis therein, one or more securement elements configured to secure the body to the penis, and a conduit in fluid communication with the chamber.

In an embodiment, a method of collecting fluid from a male includes positioning a head of a penis of a user within a chamber defined by a body of a fluid collection device. The method also may include securing the body to the penis with one or more securement elements. The method also may include receiving fluids discharged from the penis into the chamber of the fluid collection device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are directed to systems and methods including a male fluid collection device and a securement element configured to secure the fluid collection device to a penis. Conventional male fluid collection devices can be difficult to retain on the penis during use. The embodiments of male fluid collection devices disclosed herein include external catheters for men that may be used as alternatives to condom catheters. The male fluid collection devices also include a securement element configured to secure the male fluid collection device to the penis and retain the male fluid collection device in position to collection fluid from the user with minimal (e.g. no) leakage. The male fluid collection devices disclosed herein are configured to collect fluids from an individual, such as urine, penile discharge, reproductive fluids, blood, sweat, or other bodily fluids.

Fluid collection devices disclosed herein may be used in fluid collection systems. The fluid collection systems may include a fluid collection device, a fluid storage container, and a portable vacuum source. Fluid (e.g., urine or other bodily fluids) collected in the fluid collection device may be removed from the fluid collection device via a conduit which is in fluid communication with a chamber or an interior region of the fluid collection device. For example, a first open end of the conduit may extend into or have direct fluid communication with the chamber of the fluid collection device. The second open end of the conduit may extend into the fluid storage container or the portable vacuum source.

The suction force may be introduced into the interior region of the fluid collection device via the first open end of the conduit responsive to a suction (e.g., vacuum) force applied at the second end of the conduit. The suction force may be applied to the second open end of the conduit by the portable vacuum source either directly or indirectly.

In some embodiments, the portable vacuum source may be disposed in or on the fluid collection device. In such embodiments, the conduit may extend from the fluid collection device and attach to the portable vacuum source at a first point therein. An additional conduit may attach to the portable vacuum source at a second point thereon and may extend out of the fluid collection device, and may attach to the fluid storage container. Accordingly, a vacuum (e.g., suction) may be drawn through the fluid collection device via the fluid storage container. Fluid, such as urine, may be drained from the fluid collection device using the portable vacuum source.

Figure 1:
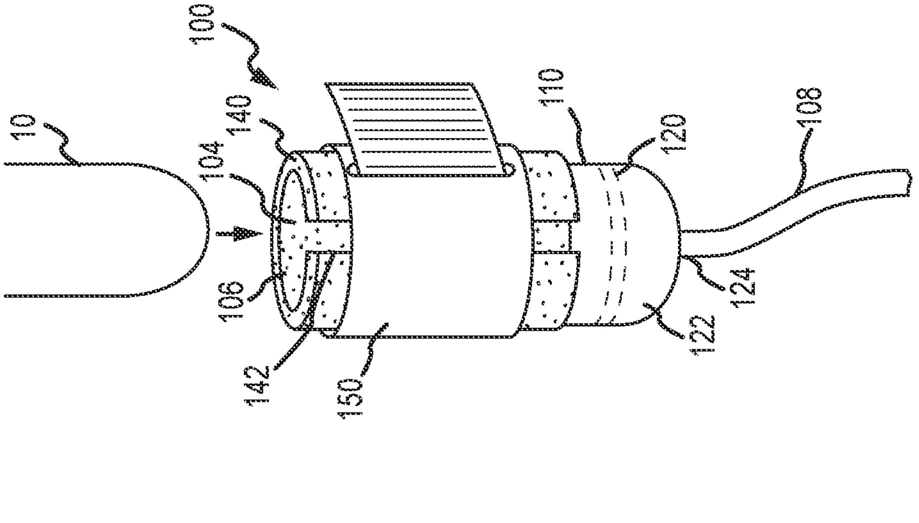
FIG. 1 is an isometric view of a male fluid collection device, according to an embodiment.

In many embodiments, a male fluid collection device includes a body, one or more securement elements, and a conduit. The body defines a chamber that is sized to receive at least a head of a penis therein. The one or more securement elements are configured to secure the body to the penis and the conduit is in fluid communication with the chamber. FIG. 1 is an isometric view of a fluid collection device 100 including a body having a tubular portion 140 and a fluid impermeable cap 110 secured to the tubular portion 140, a securement element 150, and a conduit 108. The tubular portion 140 may include a foam material, such as an open cell foam. In some embodiments, the foam material includes an open cell hydrophobic foam material. The foam material allows air into the system when vacuum is pulled through the conduit 108, preventing undesirable suction directly on the skin of the penis 10.

The tubular portion 140 may include a material, such as a foam material, having a low durometer that is soft when contacting the penis. For example, the material of the tubular portion 140 may have a shore A durometer of less than about 30, less than about 25, less than about 20, less than about 15, less than about 10, about 10 to about 30, about 10 to about 20, about 15 to about 25, about 20 to about 30, about 10 to about 15, about 15 to about 20, about 20 to about 25, or about 25 to about 30. The material of the tubular portion 140 also may include a high compression material.

The tubular portion 140 may include a C-shaped cross-section that has a slit 142 or gap that may be closed when tightened by the securement element 150 to form an O-shaped tubular element. In some embodiments, the tubular portion 140 includes an O-shaped cross-section whether or not the securement element 150 has tightened around the tubular portion 140 (e.g., the slit or gap is absent from the tubular portion). The tubular portion 140 may define at least a portion of the chamber 104. In some embodiments, both the tubular portion 140 and the cap 110 may together define at least a portion of the chamber 104. The tubular portion 140 also defines or may otherwise include an opening 106 leading to the chamber 104. The opening 106 and the chamber 104 are sized and dimensioned to receive at least the head of the penis 10 when at least a portion of the penis 10 is inserted into the fluid collection device 100 through the opening 106. The opening 106 and the chamber 104 may be sized and dimensioned to generally interface the penis 10 as the penis is inserted into the fluid collection device through to opening 106. In use, the tubular portion 140 may be positioned around and/or interface at least a portion of the head of the penis 10 and/or at least a portion of the shaft of the penis 10 when the securement element 150 tightens around the tubular portion 140.

The cap 110 is fluid impermeable and secured to the tubular portion 140. In some embodiments, the cap 110 may be secured to the tubular portion with one or more of an adhesive, chemical bonding, welding (e.g., radio frequency welding or ultrasonic welding), mechanically (e.g., clips or spikes), or friction fit. The cap 110 may temporarily store the fluids in a chamber 104 defined by the cap 110. The cap 110 may be formed of any suitable fluid impermeable materials, such as a fluid impermeable polymer (e.g., silicone, polypropylene, polyethylene, polyethylene terephthalate, a polycarbonate, etc.), polyurethane films, thermoplastic elastomer (TPE), rubber, thermoplastic polyurethane, another suitable material, or combinations thereof. As such, the cap 110 substantially prevents the fluids from exiting the portions of the chamber 104 that are spaced from the opening 106. The cap 110 may be flexible, thereby enabling the fluid collection device 100 to bend or curve when positioned against the body of a wearer. Example fluid impermeable materials may include, but are not limited to, a fluid impermeable material including at least one of Versaflex CL 2000X TPE, Dynaflex G6713 TPE, or Silpuran 6000/05 A/B silicone. In some embodiments, the cap 110 may be generally rigid.

In some embodiments, the cap 110 may define an aperture 124 sized to receive the conduit 108 (e.g., at least one tube). The aperture 124 may be generally opposite to the opening 106. The at least one conduit 108 may be disposed in or have communication with the chamber 104 via the aperture 124. The aperture 124 may be configured to form an at least substantially fluid tight seal against the conduit 108 or the at least one tube thereby substantially preventing the fluids from escaping the chamber 104.

The cap also may include a fluid permeable layer 120 positioned in the chamber 104 of the cap 110 to be adjacent and/or interface the urethra opening on the head of the penis 10. The fluid permeable layer 120 may cover or extend across at least a portion (e.g., all) of the chamber 104 in the cap 120. The fluid permeable body 120 may be configured to wick any fluid away from the penis 10 and the opening 106, thereby preventing the fluid from escaping the chamber 104. The fluid permeable layer 120 also may wick the fluid generally towards the conduit 108.

The fluid permeable layer 120 may include any material that may wick the fluid. The permeable properties referred to herein may be wicking, capillary action, diffusion, or other similar properties or processes, and are referred to herein as “permeable” and/or “wicking.” Such “wicking” or other physical properties may exclude absorption into the fluid permeable layer 120, such as not include absorption of the bodily fluid into the fluid permeable layer 120. Put another way, substantially no absorption or solubility of the bodily fluids into the material may take place after the material is exposed to the bodily fluids and removed from the bodily fluids for a time. While no absorption or solubility is desired, the term “substantially no absorption” may allow for nominal amounts of absorption and/or solubility of the bodily fluids into the fluid permeable body 120 (e.g., absorbency), such as less than about 30 wt % of the dry weight of the fluid permeable body 110, less than about 20 wt %, less than about 10 wt %, less than about 7 wt %, less than about 5 wt %, less than about 3 wt %, less than about 2 wt %, less than about 1 wt %, or less than about 0.5 wt % of the dry weight of the fluid permeable body 210. In an embodiment, the fluid permeable body 210 may include at least one absorbent or adsorbent material.

The fluid permeable layer 120 may include a one-way fluid movement fabric. As such, the fluid permeable layer 120 may remove fluid from the area around the penis 10, thereby leaving the penis 10 dry. The fluid permeable layer 120 may enable the fluid to flow generally towards a reservoir 122 of void space formed within the chamber 104. For example, the fluid permeable layer 120 may include a porous or fibrous material, such as hydrophilic polyolefin. In some embodiments, the fluid permeable layer 120 consists of or consists essentially of a porous or fibrous material, such as hydrophilic polyolefin. Examples of polyolefin that may be used in the fluid permeable layer 120 include, but are not limited to, polyethylene, polypropylene, polyisobutylene, ethylene propylene rubber, ethylene propylene diene monomer, or combinations thereof. The fluid permeable layer 120 may include varying densities or dimensions. Moreover, the fluid permeable layer 120 may be manufactured according to various manufacturing methods, such as molding, extrusion, or sintering.

In some embodiments, the fluid permeable layer 120 includes a singular and porous layer. In other embodiments, the fluid permeable layer 120 may include two or more layers of fluid permeable materials. For example, the fluid collection device 100 may include a fluid permeable membrane covering at least a portion of a fluid permeable layer, with both the fluid permeable membrane and the fluid permeable layer being disposed in the chamber 104. The fluid permeable membrane may be configured to wick any fluid away from the opening 106 and the penis 10, thereby preventing the fluid from escaping the chamber 104. The permeable properties referred to herein may be wicking, capillary action, diffusion, or other similar properties or processes, and are referred to herein as "permeable" and/or "wicking." In some embodiments, at least one of the fluid permeable membrane or the fluid permeable support include nylon configured to wick fluid away from the opening 106 and the penis 10. The material of the fluid permeable membrane and the fluid permeable support also may include natural fibers. In such examples, the material may have a coating to prevent or limit absorption of fluid into the material, such as a water repellent coating.

The fluid permeable membrane may also wick the fluid generally towards the reservoir 122 and/or the conduit 108. The fluid permeable membrane may include any material that may wick the fluid. For example, the fluid permeable membrane may include fabric, such as a gauze (e.g., a silk, linen, polymer based materials such as polyester, or cotton gauze), another soft fabric (e.g., jersey knit fabric or the like), or another smooth fabric (e.g., rayon, satin, or the like). Forming the fluid permeable membrane from gauze, soft fabric, and/or smooth fabric may reduce chaffing caused by the fluid collection device 100. Other embodiments of fluid permeable membranes, fluid permeable supports, chambers, and their shapes and configurations are disclosed in U.S. patent application Ser. No. 15/612,325 filed on Jun. 2, 2017; U.S. patent application Ser. No. 15/260,103 filed on Sep. 8, 2016; U.S. patent application Ser. No. 15/611,587 filed on Jun. 1, 2017; PCT Patent Application No. PCT/US19/29608, filed on Apr. 29, 2019, the disclosure of each of which is incorporated herein, in its entirety, by this reference. In many embodiments, the fluid permeable layer 120 includes a fluid permeable support including a porous spun nylon fiber structure and a fluid permeable wicking membrane including gauze at least partially enclosing the spun nylon fiber structure. For example, the fluid permeable layer 120 may include a gauze or other wicking fabric positioned to contact the skin of the user through the opening 106. In some embodiments, the gauze or other wicking fabric is wrapped around a body of spun nylon fibers material and/or covering both sides of a substantially planar spun nylon fibers material. In some embodiments, the gauze or other wicking fabric covers the side of substantially planar spun nylon fibers material that is oriented towards the skin of the user.

In the illustrated embodiment, the conduit 108 is direct fluid communication with the chamber 104. For example, the conduit 108 may extend at least partially into the chamber 104 in the cap 110 through conduit 124. The aperture 124 may be configured to form an at least substantially fluid tight seal against the conduit 108 or the at least one tube thereby substantially preventing the fluids from escaping the chamber 104 (e.g., the reservoir 122). The conduit may be generally flush or recessed from an inner surface of the cap 110. In some embodiments, the cap 110 includes a port defining the aperture 124, and conduit may be configured to detachably secure to the port. For example, the port may protrude from the cap 110 distal to the tubular portion 140 and the conduit 108 may slide onto and off of the port. The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some embodiments, the conduit 108 may include silicone or latex.

The cap 110 may store fluids in the reservoir 122 therein. The reservoir 122 may be an unoccupied portion of the chamber 104 and is void of other material. In some embodiments, the reservoir 122 is defined at least partially by the fluid permeable layer 120 and the cap 110. In some embodiments, the reservoir 122 is absent, and the fluid permeable layer 120 extends continuously from within the chamber 104 to the aperture 124 and/or fill substantially all of the cap 110. In use, the fluid permeable layer 120 may extend continuously in the chamber from the penis 10 to the aperture 124.

The cap 110 may be sized and dimensioned to receive at least a portion of the head of the penis 10. In some embodiments, the cap 110 is sized to receive the head of the penis 110 and at least a portion of the shaft of the penis 10. When received into the chamber 104 of the cap 110, at least a portion of the penis 10 may interface at least a portion of the cap 110 and/or the fluid permeable layer 120.

The securement element 150 is configured to position around to interface the tubular portion 140. The securement element 150 is configured to allow "on the fly" or personalized adjustment of the securement element 150 during use. In some embodiments, the securement element 150 is adjustable strap, such as an elastic adjustable strap, a strap having a hose clamp, a strap having hook and loop fastener materials, one or more fasteners, a clip, a buckle, a strap having one or more adhesive portions, or combinations thereof. In some embodiments, the securement element 150 may include an O-ring.

In operation, the penis may be inserted into the tubular portion 140. In some embodiments, the penis 10 may be inserted into the tubular portion 140 and at least partially into the cap 110. In some embodiments, the penis 10 may be inserted only into the tubular portion 140, e.g., the penis 10 is absent from the cap 110 after insertion. The securement element 150 may then be tightened around the tubular portion 140 to secure the fluid collection device 100 to the penis 10. Thereafter, when urine is discharged from the penis 10, the fluid permeable layer 120 may wick the urine away from the penis 10 towards the reservoir 122 and aperture

124, and a vacuum may pull the urine out of the fluid collection device 100 through the conduit 108.

Figure 2:
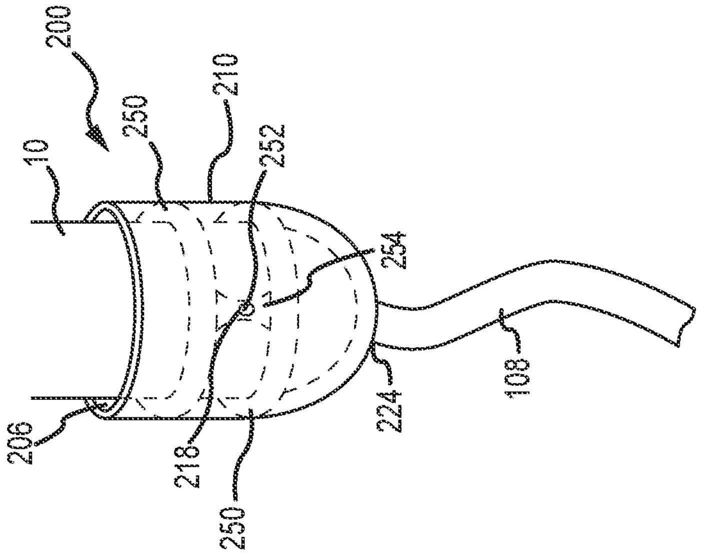
FIG. 2 is an isometric view of a male fluid collection device, according to an embodiment.
Figure 3B:
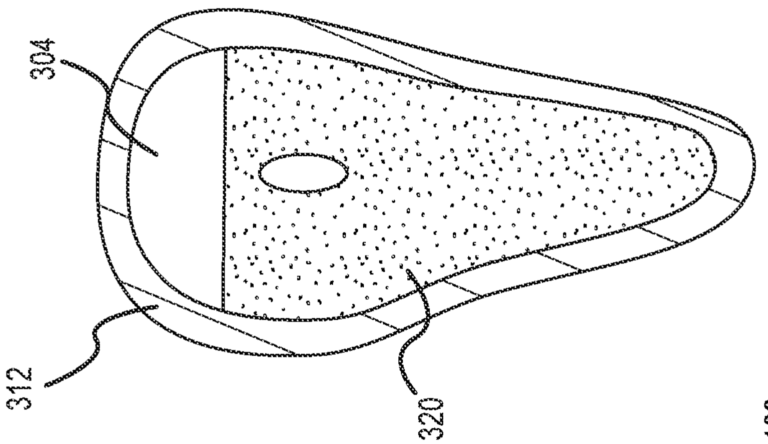
FIG. 3B is a rear view of the male fluid collection device of FIG. 3A.
Figure 3A:
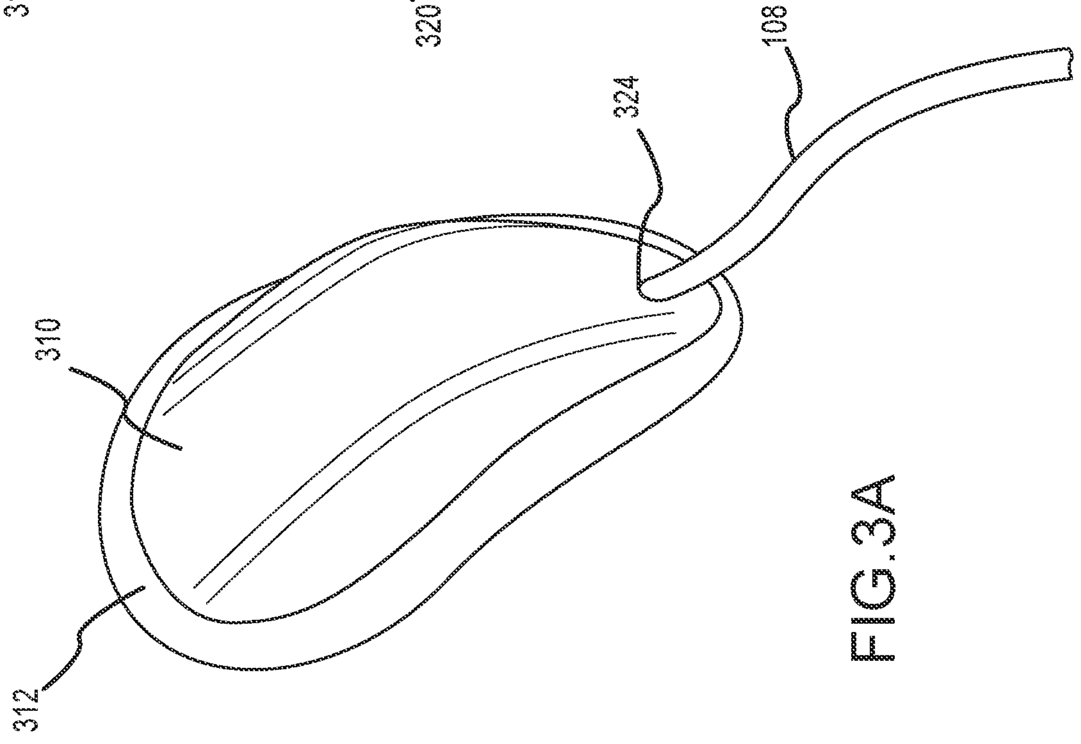
FIG. 3A is an isometric front view of a male fluid collection device, according to an embodiment.
Figure 3D:
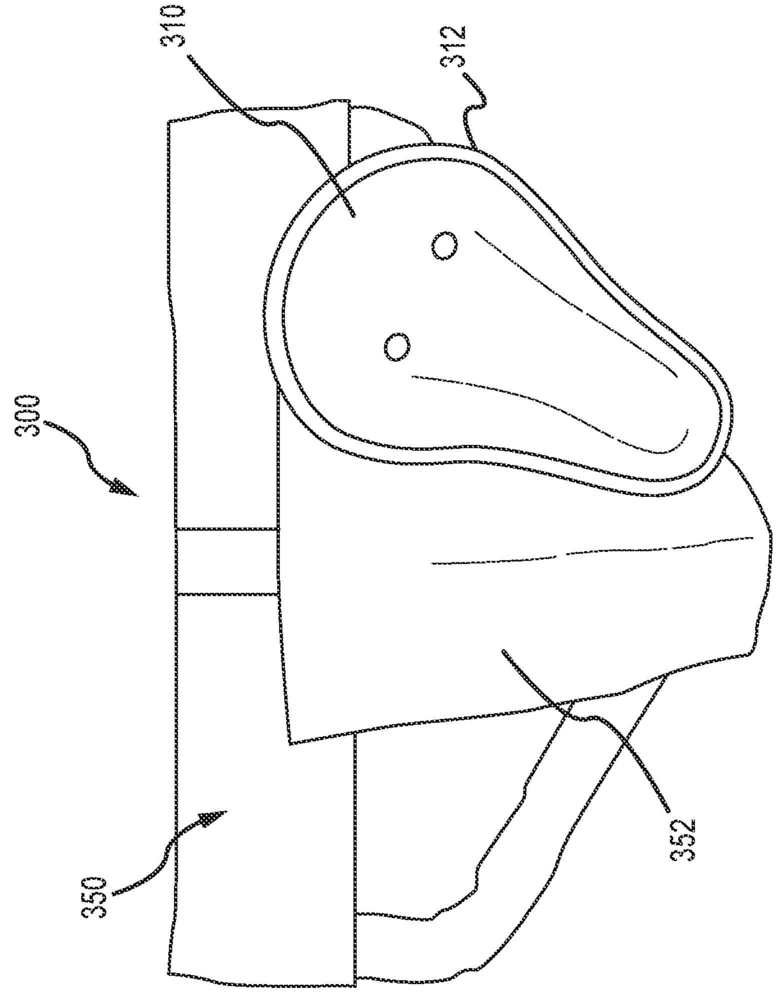
FIG. 3D is a front view of the male fluid collection device of FIG. 3A and a securement element, according to an embodiment.
Figure 3C:
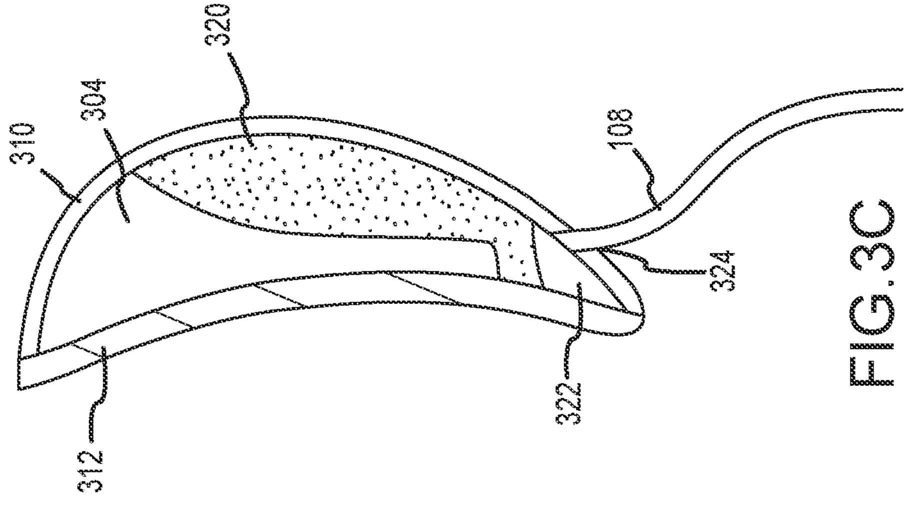
FIG. 3C is a cross-sectional side view of the male fluid collection device of FIG. 3A.

FIG. 2 is an isometric view of a fluid collection device 200 including a body 210 having an opening 206 and an aperture 224 opposite to the opening 206, a securement element, and a conduit 108. The body 210 may include a fluid impermeable layer, such as any of the materials described above in relation to the cap 110. The body 210 may define or otherwise include the chamber that is sized and dimensioned to receive at least a portion of the head of the penis 10. In some embodiments, chamber is sized and dimensioned to receive the head and at least a portion of the shaft of the penis 10. The opening 206 of the body 210 leads to the chamber and is sized and dimensioned to receive at least a head of the penis 10. The aperture 224 is configured to receive the conduit 108, thereby providing fluid communication between the chamber of the body 210 and the conduit 108. In some embodiments, the body 210 includes a thin film layer. For example, the body 210 may include a polyethylene or polyethylene film. The body also may include a through hole 218 that may be positioned between the aperture 224 and the opening 206. The through hole 218 may be sized and dimensioned for receiving at least a portion of a valve 252 therein.

The securement element includes one or more (e.g., two) inflatable rings 250 secured or securable to the body 210 and including the valve 252. The one or more inflatable rings 250 may include inflatable silicone O-rings or any other inflatable ring. The valve 252 may be positioned or positionable at least partially in the through hole 218 and is configured to receive air to inflate the one or more inflatable rings 250 and exhaust air to deflate the one or more inflatable rings 250. In some embodiments, the valve 252 includes a fixed pressure regulator, and air pressure to the one or more inflatable rings 250 may be regulated through the valve 252. A fixed pressure regulator allows the one or more inflatable rings 250 to exert the same desired (low) pressure on the penis 10, regardless of the size of the penis 10. In some embodiments, the valve 252 may receive air from an air line at the care facility or a standard syringe. In embodiments having two or more inflatable rings 250, the fluid collection device 200 may include a connector 254 in fluid communication with the valve 252 and the two inflatable rings 250 such that the two inflatable rings 250 may be inflated through a single valve 252.

Inflation of the one or more inflatable rings 250 decreases an inner diameter of one or more inflatable rings 250 effective to secure the body 210 to the penis 10. Accordingly, once the penis 10 is inserted into the chamber of the body 210, the one or more inflatable rings 250 may be inflated to complement the size of the particular penis 10. In some embodiments, the one or more inflatable rings 250 are secured to the body 210 within the chamber of the body 210. In some embodiments, the one or more inflatable rings 250 are separable from the body 210. That is, the one or more inflatable rings 250 may be positioned on the penis before or after the penis 10 is inserted into the chamber of the body 210. For example, the one or more inflatable rings 250 may be positioned on the penis 10 before inflation of the one or more inflatable rings 250 and then the penis 10 (with the one or more inflatable rings 250) may be inserted into the chamber of the body 210. Once the penis 10 is in the chamber of the body 210, the one or more rings 250 may be inflated to the desired inflation level. When inflated to a proper level, the one or more inflatable rings 250 may secure the body 210 to the penis 10 and also form a seal between a distal portion of the chamber and the opening 206, thereby preventing urine or other discharged fluids from exiting the chamber of the body through the opening 206. In embodiments having the one or more inflatable rings 250 within the chamber during use, the body 210 also may define or otherwise include an inflation inlet allowing access and/or fluid communication to the valve 252. In some embodiments, the one or more inflatable rings 250 may be positioned outside the chamber on an outer surface of the body 210.

Although not shown in in FIG. 2, in some embodiments, the fluid collection device 200 includes a fluid permeable layer 120 and/or a reservoir 122 in the chamber of the body 210, as described above in relation to the fluid collection device 100. The fluid permeable layer may extend at least to an inflatable ring of the one or more inflatable rings 250. The inflatable ring may be positioned between the fluid permeable layer and the body 210, or the fluid permeable layer may be positioned between the inflatable ring and the fluid impermeable layer.

A fluid collection system 300 is shown in FIGS. 3A-3D, according to an embodiment. The fluid collection system 300 includes a cup-shaped body 310 (such as a cricket box cup) and a securement element of a garment 350 (shown in FIG. 3D). The cup-shaped body 310 defines or otherwise includes a chamber 304 that is sized to receive at least the penis 10 therein. In some embodiments, the cup-shaped body 310 includes a chamber 304 sized to receive the penis 10 and the testicles of the users therein. The cup-shaped body 310 may be advantageous to conventional male fluid collection devices because one size may fit most sizes of male anatomy. The cup-shaped body 310 may include a fluid impermeable material, including any of the materials described above in relation to the cap 110. In some embodiments, the cup-shaped body 310 includes a semi-rigid plastic material, a soft silicone material, a closed cell foam, or combinations thereof.

The cup-shaped body 310 also includes a perimeter and an open cell foam seal 312 on the perimeter. The open cell foam seal 312 may be configured to allow air into the chamber 304 but prevent fluid from exiting the chamber through the open cell foam seal 312. In some embodiments, the open cell foam seal 312 includes a hydrophobic open cell foam seal 312. The cup-shaped body 310 also may define or otherwise include an aperture 324 configured to receive the conduit 108 effective to provide fluid communication between the chamber 304 and the conduit 108.

A fluid permeable material 320 may be positioned within the chamber 304 and configured to direct fluid discharged from the penis to the conduit 108 for removal from the chamber 304. The fluid permeable material 320 may include any of the fluid permeable materials described above in relation to the fluid permeable layer 120, including a wicking material. In some embodiments, the fluid permeable material 320 may form a coating on an interior surface of at least a portion (e.g., all) of the cup-shaped body. In some embodiments, a bottom portion of the fluid permeable material 320 includes a lip, and a reservoir 322 of void space is formed in the chamber 304. The reservoir 322 may be defined at least partially by one or more of the cup-shape body 310, the fluid permeable material 320, and/or the seal 312. The conduit 108 may be in direct fluid communication with the reservoir 322 such that urine directed from the fluid permeable material 320 to the reservoir 322 may be evacuated with the conduit 108.

The securement element of the fluid collection system 300 includes a garment 350 having one or more bands configured to wrap around the user and a support material 352 attached to the one or more straps and configured to secure the body 310 between the support material 352 and the user. For example, the garment 350 may include a jock strap garment. The garment 350 may be washable and reusable.

Figure 4B:
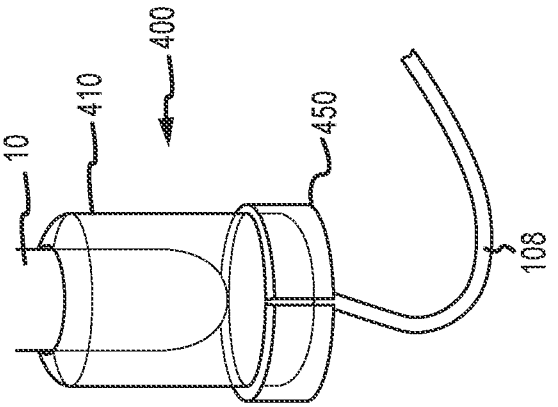
FIG. 4B is an isometric view of the male fluid collection device of FIG. 4B with a penis secured partially therein.
Figure 4A:
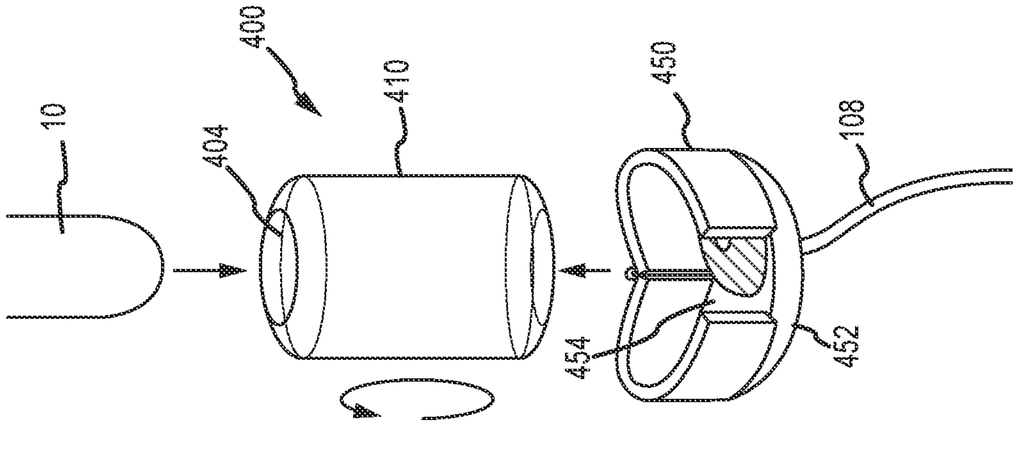
FIG. 4A is an exploded isometric view of a male fluid collection device, according to an embodiment.

A fluid collection device 400 is shown in FIGS. 4A and 4B, according to an embodiment. In the fluid collection device 400, the body includes a tubular body 410 and the securement element includes at least a clip 450 configured to clip around at least a portion of the tubular body 410. The tubular body 410 includes a chamber 404 sized to receive and interface the penis therein. In some embodiments, the tubular body 410 includes a fluid impermeable barrier housing a liquid or gel and the chamber 404 includes a passage way extending through the tubular body. The fluid impermeable barrier may include a thin film, such as a polyurethane or a polyethylene film. The tubular body 410 may be configured to roll onto the penis 10 as the penis 10 is inserted into the chamber 410 and interfaces a portion of the tubular body 410 within the chamber 404 to position at least a portion of the penis 10 in the chamber 404. In some embodiments, the tubular portion 410 includes a tube within a tube configured to roll onto the penis. FIG. 4A shows the tubular body 410 before the penis 10 has been inserted into the chamber 404, and FIG. 4B shows the tubular body 410 after the penis 10 has been inserted into the chamber 404 and the tubular body 410 has been rolled onto the penis 10. Because the tubular body 410 is configured to roll onto the penis 10, a portion of the tubular body 410 initially on an outer surface of the tubular body 410 may be rolled to be an inner surface of the tubular body 410 and partially define the chamber 404 when the tubular body 410 is rolled onto the penis 10.

In some embodiments, the tubular body 410 includes a fluid permeable material positioned on the tubular body 410. The fluid permeable material may include any of the fluid permeable materials described above in reference to the fluid permeable layer 120. The fluid permeable material may be positioned on the tubular body 410 to interface and move with the head of the penis 10 as the penis 10 is inserted into the chamber 405. Once the tubular body 410 is secured to the penis 10 with the clip (shown in FIG. 4B), the fluid permeable material may wick fluid away from the penis 10 towards the conduit 108.

The clip 450 may be configured to clip or otherwise secure around at least a portion of the tubular body 410 and stop the tubular body 410 from rolling when the penis 10 is positioned at a desired positioned within the chamber 404 of the tubular body 410 effective to secure the tubular body 410 to the penis 10. The fluid collection device 400 also may include a sump 452 secured to at least one of the clip 450 or the tubular body 410. The sump 452 is configured to collect fluid discharged from the penis 10 when the penis 10 is positioned within the tubular body 410 (shown in FIG. 4B). The sump 452 may include an aperture configured to receive the conduit 108 effective and provide fluid communication between the chamber 404 and the conduit 108. In some embodiments, the sump 452 includes a fluid impermeable layer defining the aperture. The fluid impermeable layer may include any of the fluid impermeable materials described above in relation to the cap 110. The sump 452 also includes a fluid permeable material 454 positioned on the fluid impermeable layer and configured to wick fluid towards the aperture. The fluid permeable material 454 may include any of the fluid permeable materials described above in relation to the fluid impermeable layer 120.

Figure 5A:
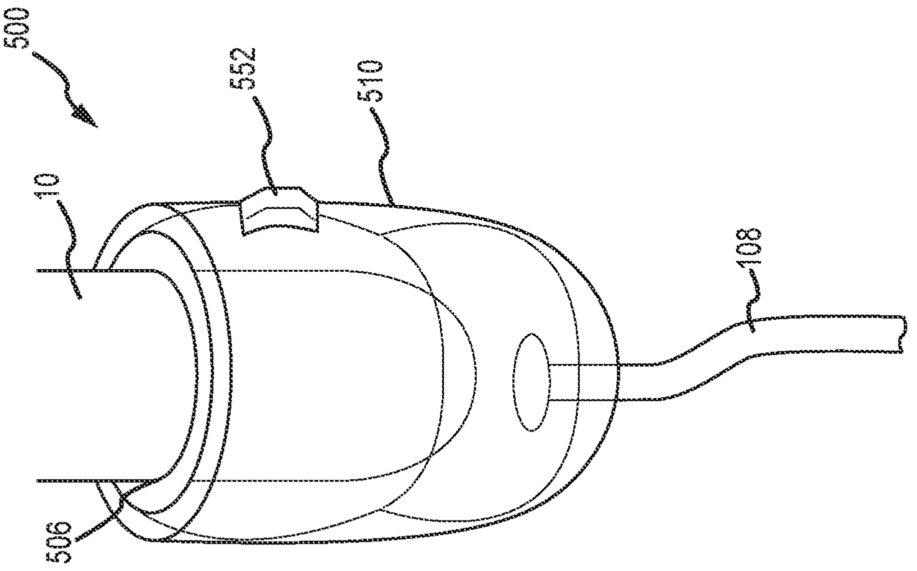
FIG. 5A is an isometric view of a male fluid collection device, according to an embodiment.
Figure 5B:
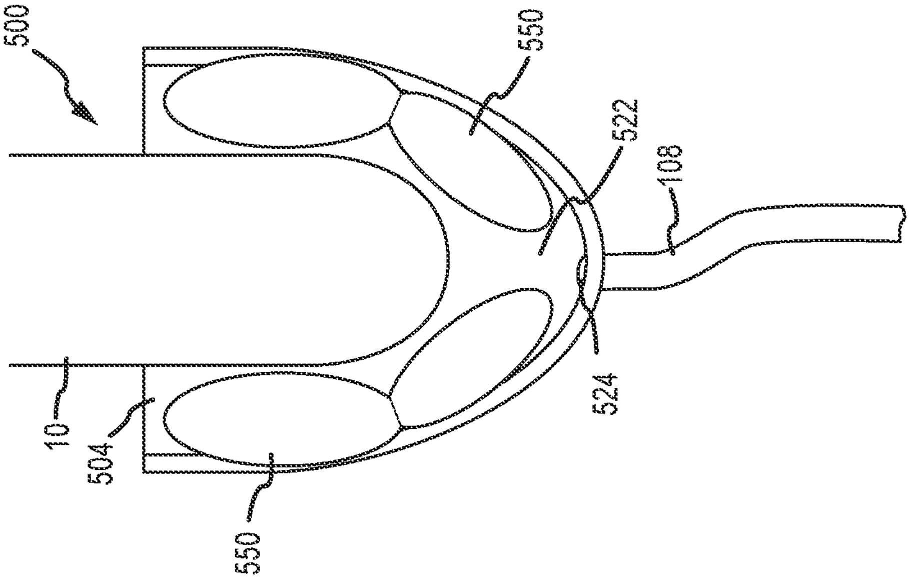
FIG. 5B is a cross-sectional isometric view of the male fluid collection device of FIG. 5A.

A fluid collection device 500 is shown in FIGS. 5A and 5B, according to an embodiment. FIG. 5A shows an isometric view of the fluid collection device 500 and FIG. 5B shows a cross-sectional view of the fluid collection device 500 of FIG. 5A. The body of the fluid collection device 500 includes at least a fluid impermeable layer 510. The fluid impermeable layer 510 may include any of the materials described above in relation to the cap 110. In some embodiments, the fluid impermeable layer 510 includes a fluid impermeable film, such as a polyurethane, polyethylene, polyester, or polypropylene film. A chamber 504 may be positioned within and/or at least partially defined by the fluid impermeable layer 510. The chamber 504 is sized and dimensioned to receive at least a portion of the head of the penis 10. In some embodiments, the chamber 504 is sized and dimensioned to receive the head and at least a portion of the shaft of the penis 10. The body of the fluid collection device 500 also includes an opening 506 that leads to the chamber 504 and is sized and dimensioned to receive at least the head of the penis 10. The body also includes an aperture 524 distal to the opening 506 and configured to receive the conduit 108 effective to provide fluid communication between the chamber 504 and the conduit 108. The body also may include an inflation inlet positioned on the fluid impermeable layer 510 to provide fluid communication with a valve 552.

In the fluid collection device 500, the one or more securement elements include one or more inflatable bags 550 positioned within the chamber 504. The fluid collection device 500 also may include a valve 552 to receive air to inflate the one or more inflatable bags 550 and exhaust air to deflate the one or more inflatable bags 550. In some embodiments, the valve 552 includes a fixed pressure regulator and air pressure to the one or more inflatable bags 550 may be regulated through the valve 552. A fixed pressure regulator allows the one or more inflatable bags 550 to exert the same desired (low) pressure on the penis 10, regardless of the size of the penis 10. In some embodiments, the valve 552 may receive air from an air line at the care facility or a standard syringe. In embodiments having two or more inflatable bags 550, the two or more inflatable bags 550 may be in fluid communication with one another such that pressure in the two or more inflatable bags 550 may be equalized around the penis 10.

Inflation of the one or more inflatable bags 550 decreases an inner diameter of one or more inflatable bags 550 effective to secure the body of the fluid collection device 500 to the penis 10. Accordingly, once the penis 10 is inserted into the chamber 504, the one or more inflatable bags 550 may be inflated to complement the size of the particular penis 10. With the penis 10 inserted into the chamber 504 and the one or more inflatable bags 550 at least partially inflated, the one or more inflatable bags 550 may interface at least one of the head or the shaft of the penis 10. In some embodiments, the one or more inflatable bags 550 are secured to the body of the fluid collection device 500 within the chamber 504. In some embodiments, the one or more inflatable bags 550 are separable from the body. That is, the one or more inflatable bags 550 may be positioned on the penis before or after the penis 10 is inserted into the chamber 504. For example, the one or more inflatable bags 550 may be positioned on the penis 10 before inflation of the one or more inflatable bags 550 and then the penis 10 (with the one or more inflatable bags 550) may be inserted into the chamber 504. Once the penis 10 is in the chamber 504, the one or more bags 550 may be inflated to the desired inflation level. When inflated to a proper level, the one or more inflatable bags 550 may secure the body of the fluid collection device 500 to the penis 10 and also form a seal between a distal portion of the chamber 504 and the opening 506, thereby preventing urine or other discharged fluids from exiting the chamber of the body through the opening 506. In embodiments having the one or more inflatable bags 550 within the chamber 504 during use, the body of the fluid collection device 500 also may define or otherwise include an inflation inlet allowing access and/or fluid communication to the valve 552.

In some embodiments, the fluid collection device 500 includes a fluid permeable layer (not shown) and a reservoir 522 in the chamber 504, as described above in relation to the fluid collection device 100. The fluid permeable layer may extend at least to an inflatable bag of the one or more inflatable bags 550. The inflatable bag may be positioned between the fluid permeable layer and the body of the fluid collection device 500, or the fluid permeable layer may be positioned between the inflatable bag and the fluid impermeable layer 510.

Figure 6A:
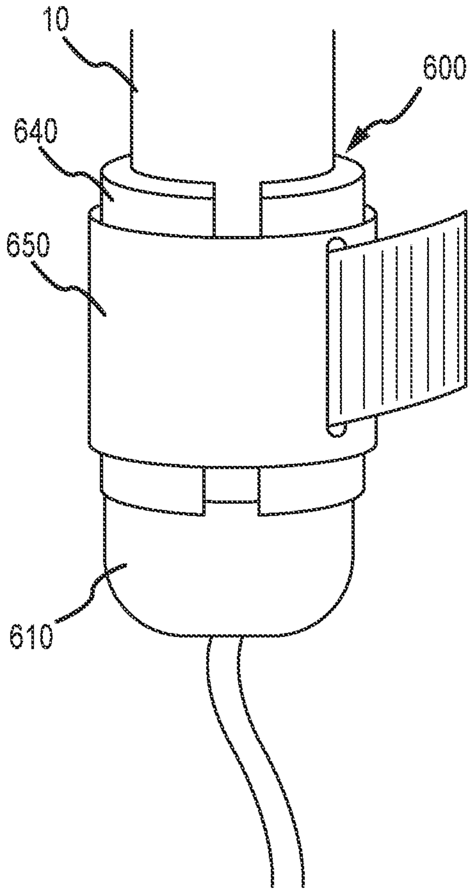
FIG. 6A is an isometric view of a male fluid collection device, according to an embodiment.
Figure 6B:
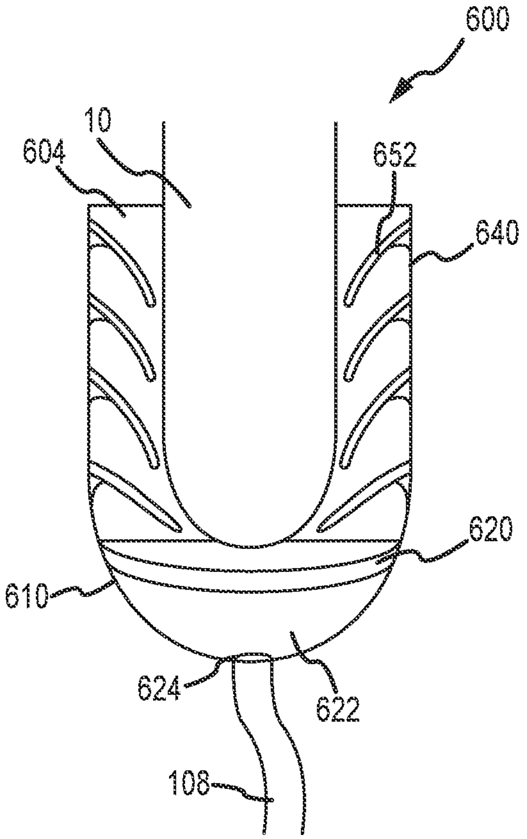
FIG. 6B is a cross-sectional isometric view of the male fluid collection device of FIG. 6A.

A fluid collection device 600 is shown in FIGS. 6A and 6B, according to an embodiment. FIG. 6A shows an isometric view of the fluid collection device 600 and FIG. 6B shows a cross-sectional view of the fluid collection device 600 of FIG. 6A. The body of the fluid collection device 600 includes a tubular portion 640 and a fluid impermeable cap 610 secured or securable to the tubular portion 640. Unless otherwise noted, the tubular portion 640 and the cap 610 may include any aspect of the tubular portion 140 and the cap 110 described above in relation to the fluid collection device 100. For example, the cap 610 may include a fluid impermeable cap that at least partially defines or includes the chamber 604 and an aperture 624. The tubular portion 640 also may at least partially define the chamber 604. The aperture 624 is configured to receive the conduit 108 effective to provide fluid communication between the chamber 604 and the conduit 108. In some embodiments, the tubular portion 640 includes any of the fluid impermeable materials described herein. For example, the tubular portion 640 may include at least one of elastomer, a silicone, a thermoplastic elastomer, thermoplastic polyurethane, or any combination thereof. The body of the fluid collection device 600 also may include a fluid permeable layer 620 and a reservoir 622. The fluid permeable layer 620 and the reservoir 622 may include any aspect of the fluid permeable layer 120 and the reservoir 122 described above in relation to the fluid collection device 100.

In some embodiments, the tubular portion 640 includes a plurality of projections 652 extending inwardly from an inner surface of the tubular portion 640. The plurality of projections 652 may include a plurality of retention or detent elements, tabs, fins, or barbs. The plurality of projections 652 are sized and positioned to interface the penis 10 as the penis 10 is inserted into the chamber 604 and when at least a portion of the penis 10 is positioned within the chamber 604. In some embodiments, the plurality of projections 652 may be angled from the inner surface of the tubular portion 640 downward towards the cap 610. This angling of the plurality of projections 652 inhibits the fluid collection device 600 from accidentally moving out of position on the penis 10. To remove the fluid collection device 600 from the penis 10, the tubular portion 640 may be pinched to separate a portion of the plurality of projections 652 from the penis 10.

A material of the plurality of projections 652 may include one or more of an elastomer, a silicone, a thermoplastic elastomer, thermoplastic polyurethane, or any combination thereof. Because the plurality of projections 652 are highly flexible, the plurality of projections 652 may bend to create a larger opening within the chamber 604 to accommodate the size of the penis 10. The material of the plurality of projections 652 also may be soft, having a shore A durometer of about 20 to about 70, about 30 to about 60, about 20 to about 30, about 30 to about 40, about 40 to about 50, about 50 to about 60, about 60 to about 70, less than about 70, less than about 60, less than about 50, less than about 40, or less than about 30.

The one or more securement elements of the fluid collection device 600 may include an adjustable strap 650 positioned and configured to tighten around the tubular portion 640 to secure the body to the penis 10 when at least a portion of the penis 10 is positioned within the chamber 604. The adjustable strap 650 may include any aspect of the securement element 150 described above in relation to the fluid collection device 100. In some embodiments, the adjustable strap 650 includes an elastic adjustable strap. In some embodiments, the adjustable strap 650 includes at least one of a hose clamp, a hook and loop fastener material, or one or more fasteners.

Figure 7:
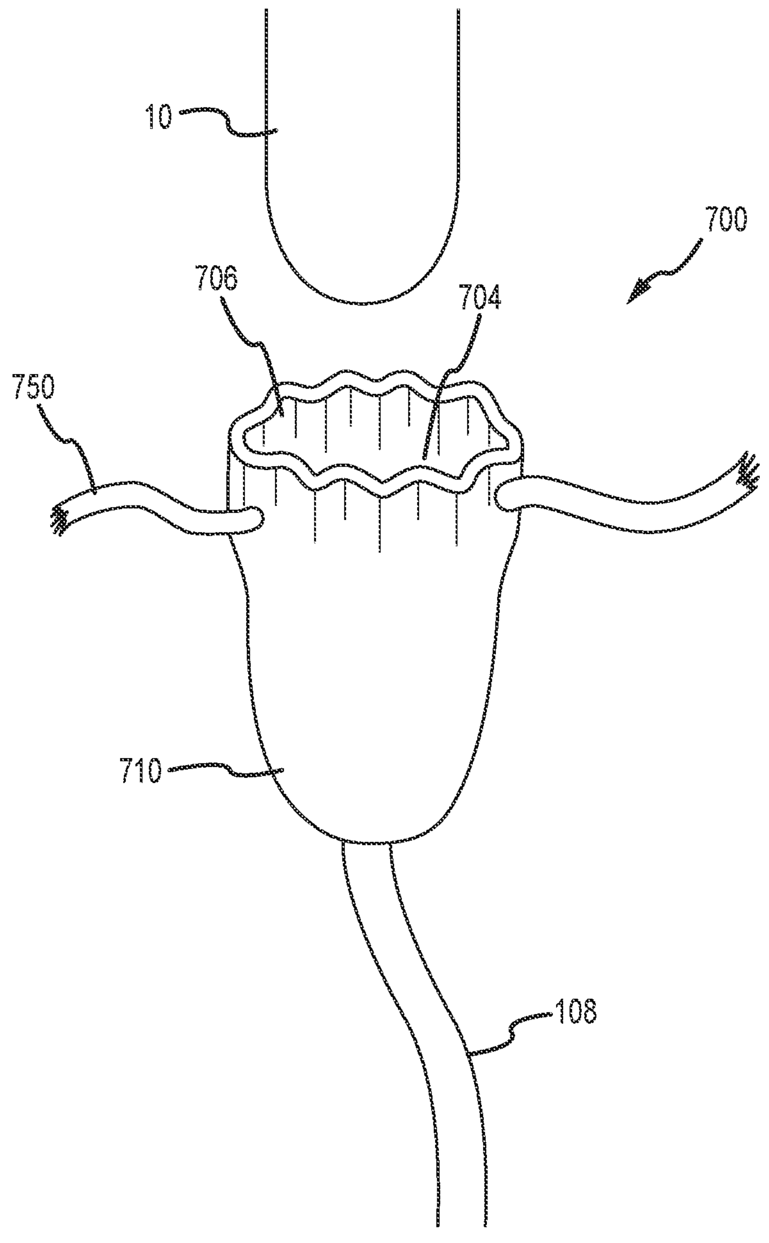
FIG. 7 is an isometric view of a male fluid collection device, according to an embodiment.

A fluid collection device 700 is shown in FIG. 7, according to an embodiment. The body of the fluid collection device 700 includes at least a fluid impermeable layer 710. The fluid impermeable layer 710 may include a pouch-like and/or cup-shaped configuration defining or otherwise including a chamber 704 and an opening 706 both sized and dimensioned to receive at least the head of the penis 10. In some embodiments, the chamber 704 in fluid impermeable layer is sized and dimensioned to receive at least the head and a portion of the shaft of the penis 10. The fluid impermeable layer 706 also may include an aperture (not visible) distal to the opening 706. The aperture in the fluid impermeable layer 706 is configured to receive the conduit 108 effective to provide fluid communication between the chamber 704 and the conduit 108.

The fluid impermeable layer 710 may include any fluid impermeable materials described herein. In some embodiments, the fluid impermeable layer 710 may include an impermeable film, such as a film include one or more of polyurethane, polyethylene, polyester, polypropylene, or combinations thereof. Though not shown in FIG. 7, some embodiments of the fluid collection device 700 include a fluid permeable layer positioned within the chamber 704 and/or a reservoir positioned in the chamber 704 adjacent to the aperture. The fluid permeable layer may extend across the chamber 704 or be adhered to at least a portion of the inner surface of the fluid impermeable layer 710.

The one or more securement elements of the fluid collection device 700 may include a drawstring 750 secured to the fluid impermeable layer 710. The drawstring 750 may be positioned proximate to the opening 706 or between the opening 706 and the aperture distal to the opening 706. The drawstring 750 may be configured to tighten the fluid impermeable layer 710 around a portion of the penis 10. For example, the drawstring 750 may be positioned in and through one or more channels around the fluid impermeable layer 710 such that the drawstring 750 may be tightened and tied around at least a portion of the fluid impermeable layer 710.

Figure 8:
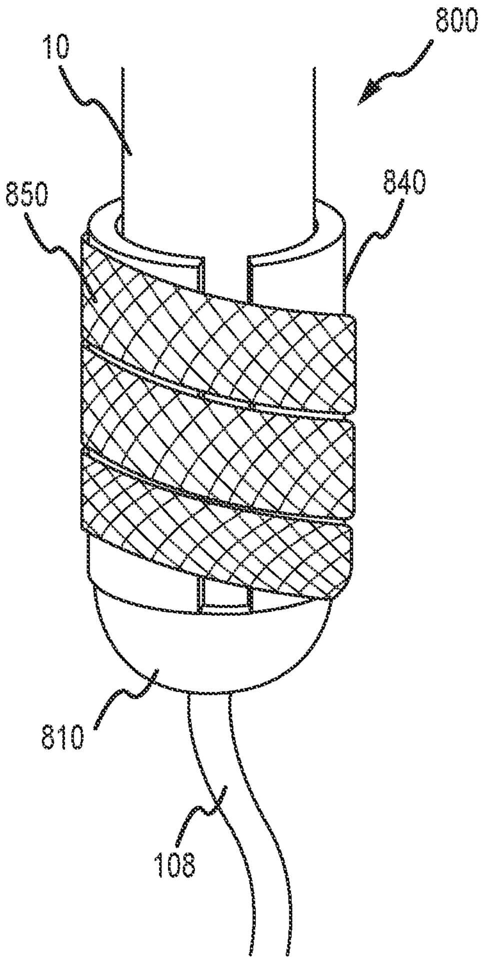
FIG. 8 is an isometric view of a male fluid collection device, according to an embodiment.

A fluid collection device 800 is shown in FIG. 8, according to an embodiment. The body of the fluid collection device 800 includes a tubular portion 840 and a fluid impermeable cap 810 secured or securable to the tubular portion 840. Unless otherwise noted, the tubular portion 840 and the cap 810 may include any aspect of the tubular portion 140 and the cap 110 described above in relation to the fluid collection device 100. For example, the cap 810 may include a fluid impermeable cap that at least partially defines or includes a chamber and an aperture. The tubular portion 840 also may at least partially define the chamber. The aperture is configured to receive the conduit 108 effective to provide fluid communication between the chamber and the conduit 108. In some embodiments, the tubular portion 840 includes any of the fluid impermeable materials described herein. For example, the tubular portion 840 may include at least one of elastomer, a silicone, a thermoplastic elastomer, thermoplastic polyurethane, or any combination thereof. In some embodiments, the tubular portion 840 includes any of the foam materials described herein, such as an open cell hydrophobic foam. In some embodiments, the tubular portion 840 includes a breathable fabric. Though not shown in FIG. 8, the body of the fluid collection device 800 also may include a fluid permeable layer and a reservoir. The fluid permeable layer and the reservoir may include any aspect of the fluid permeable layer 120 and the reservoir 122 described above in relation to the fluid collection device 100.

The one or more securement elements of the fluid collection device 800 include an adjustable hook and loop fastener strap 850 positioned and configured to tighten around the tubular portion 840 to secure the body to the penis 10 when at least a portion of the penis 10 is positioned within the chamber. The adjustable hook and loop fastener strap 850 also may include any aspect of the securement element 150 described above in relation to the fluid collection device 100. In some embodiments, the adjustable hook and loop fastener strap 850 includes an elastic adjustable hook and loop fastener strap. The adjustable hook and loop fastener strap 850 may be secured to the tubular portion 840 or separate from the tubular portion 840.

Figure 9:
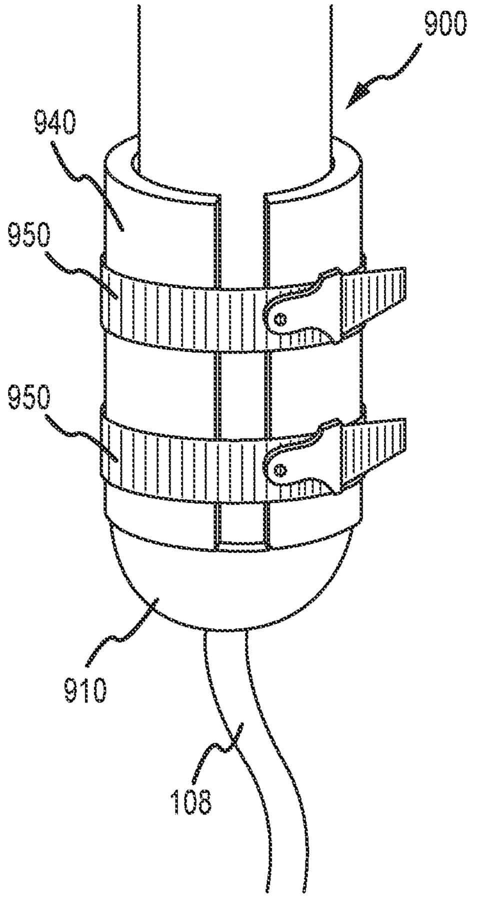
FIG. 9 is an isometric view of a male fluid collection device, according to an embodiment.

A fluid collection device 900 is shown in FIG. 9, according to an embodiment. The body of the fluid collection device 900 includes a tubular portion 940 and a fluid impermeable cap 910 secured or securable to the tubular portion 940. Unless otherwise noted, the tubular portion 940 and the cap 910 may include any aspect of the tubular body 140 and the cap 110 described above in relation to the fluid collection device 100. For example, the cap 910 may include a fluid impermeable cap that at least partially defines or includes a chamber and an aperture. The tubular portion 940 also may at least partially define the chamber. The aperture is configured to receive the conduit 108 effective to provide fluid communication between the chamber and the conduit 108. In some embodiments, the tubular portion 940 includes any of the fluid impermeable materials described herein. For example, the tubular portion 940 may include at least one of elastomer, a silicone, a thermoplastic elastomer, thermoplastic polyurethane, or any combination thereof. In some embodiments, the tubular portion 940 includes any of the foam materials described herein, such as an open cell hydrophobic foam. In some embodiments, the tubular portion 940 includes a breathable fabric. Though not shown in FIG. 9, the body of the fluid collection device 900 also may include a fluid permeable layer and a reservoir. The fluid permeable layer and the reservoir may include any aspect of the fluid permeable layer 120 and the reservoir 122 described above in relation to the fluid collection device 100.

The one or more securement elements of the fluid collection device 900 include an adjustable ratchet strap 950 positioned and configured to tighten around the tubular portion 940 to secure the body to the penis 10 when at least a portion of the penis 10 is positioned within the chamber. The adjustable ratchet strap 950 also may include any aspect of the securement element 150 described above in relation to the fluid collection device 100. In some embodiments, the adjustable ratchet strap 950 includes an elastic adjustable ratchet strap. The adjustable ratchet strap 950 may be secured to the tubular portion 940 or separate from the tubular portion 940.

Figure 10:
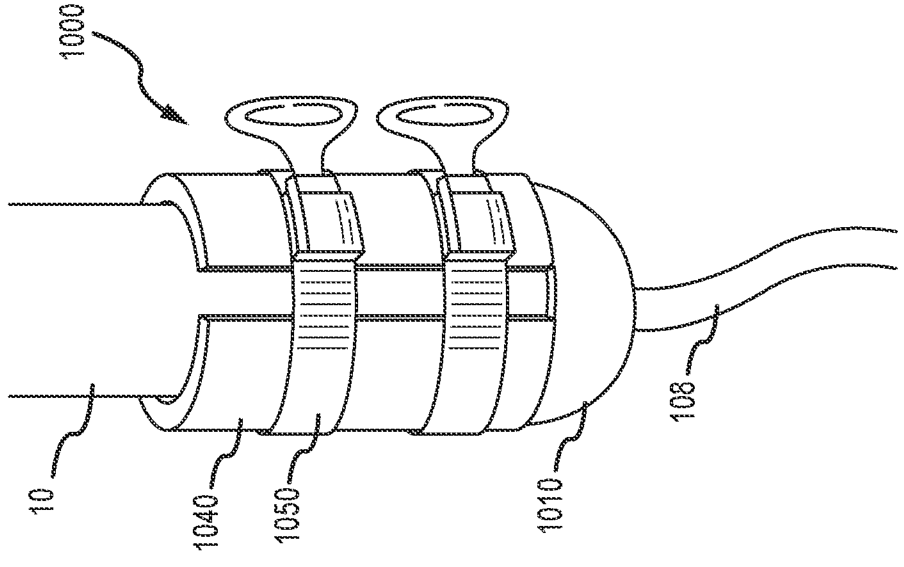
FIG. 10 is an isometric view of a male fluid collection device, according to an embodiment.

A fluid collection device 1000 is shown in FIG. 10, according to an embodiment. The body of the fluid collection device 1000 includes a tubular portion 1040 and a fluid impermeable cap 1010 secured or securable to the tubular portion 1040. Unless otherwise noted, the tubular portion 1040 and the cap 1010 may include any aspect of the tubular portion 140 and the cap 110 described above in relation to the fluid collection device 100. For example, the cap 1010 may include a fluid impermeable cap that at least partially defines or includes a chamber and an aperture. The tubular portion 1040 also may at least partially define the chamber. The aperture is configured to receive the conduit 108 effective to provide fluid communication between the chamber and the conduit 108. In some embodiments, the tubular portion 1040 includes any of the fluid impermeable materials described herein. For example, the tubular portion 1040 may include at least one of elastomer, a silicone, a thermoplastic elastomer, thermoplastic polyurethane, or any combination thereof. In some embodiments, the tubular portion 1040 includes any of the foam materials described herein, such as an open cell hydrophobic foam. In some embodiments, the tubular portion 1040 includes a breathable fabric. Though not shown in FIG. 10, the body of the fluid collection device 1000 also may include a fluid permeable layer and a reservoir. The fluid permeable layer and the reservoir may include any aspect of the fluid permeable layer 120 and the reservoir 122 described above in relation to the fluid collection device 100.

The one or more securement elements of the fluid collection device 1000 include one or more worm drive hose clamps 1050 positioned and configured to tighten around the tubular portion 1040 to secure the body to the penis 10 when at least a portion of the penis 10 is positioned within the chamber. The one or more worm drive hose clamps 1050 also may include any aspect of the securement element 150 described above in relation to the fluid collection device 100. In some embodiments, the one or more worm drive hose clamps 1050 includes one or more elastic worm drive hose clamps. The one or more worm drive hose clamps 1050 may be secured to the tubular portion 1040 or separate from the tubular portion 1040.

Figure 11A:
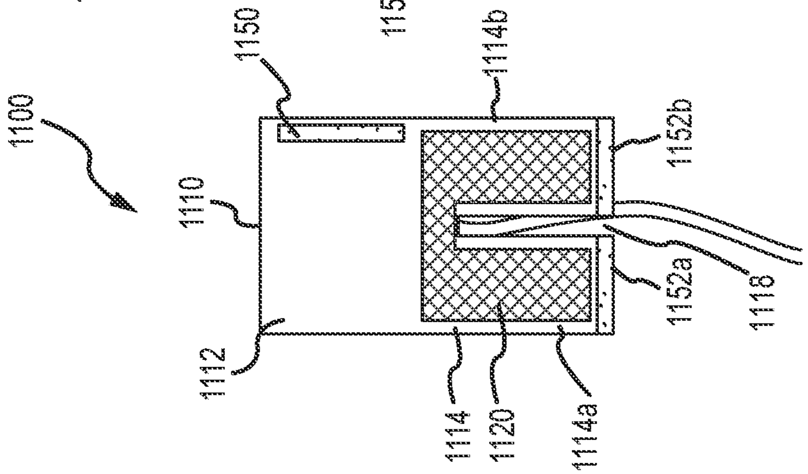
FIG. 11A is an unwrapped configuration of a male fluid collection device, according to an embodiment.
Figure 11B:
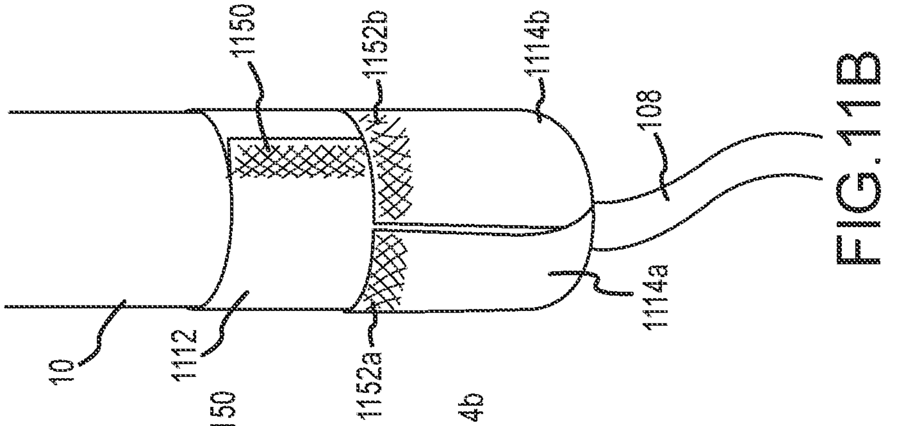
FIG. 11B is a wrapped configuration of the male fluid collection device of FIG. 11A.

A fluid collection device 1100 is shown in FIGS. 11A and 11B, according to an embodiment. The fluid collection device 1100 is configured to wrap around the penis 10. FIG. 11A is an unwrapped configuration of the fluid collection device 1100, and FIG. 11B is a wrapped configuration of the fluid collection device 1100 of FIG. 11A. The body of the fluid collection device 1100 includes a fluid impermeable layer 1110 including a first region 1112 having an inner surface and an outer surface, a second region 1114 having an inner surface and an outer surface, a slot 1118 separating two portions 1114*a*, 1114*b* of the second region 1114, and a fluid permeable layer 1120 secured to the inner surface of the two portions 1114*a*, 1114*b* of the second region 1114. The conduit 108 is positioned at least partially in the slot 1118 between the two portions 1114*a*, 1114*b* of the second region 1114. The fluid permeable layer 1120 may include any fluid permeable materials described above in relation to the fluid permeable layer 120. The fluid impermeable layer 1110 may include any fluid impermeable material described herein, including a fluid impermeable film such as a polyurethane, polyethylene, polyester, or polypropylene film.

The one or more securement elements of the fluid collection device 1100 include an adhesive strip 1150 secured to the inner surface of the first region 1112 and a different adhesive strip 1152*a*, 1152*b* secured to the inner surface of each of the two portions 1114*a*, 1114*b* of the second region 1114 distal to the first region 1112. The adhesive strips 1150, 1152*a*, 1152*b* may include any adhesive known in the art, such as an adhesive used on a diaper.

To adjust the fluid collection device from the unwrapped configuration shown in FIG. 11A to the wrapped configuration show in FIG. 11B, the first region 1112 of the body is configured to wrap around at least the head of the penis 10 with the adhesive strip 1150 of the first region 1112 positioned to secure to the outer surface of the first region 1112, thereby defining at least a portion of the chamber of the fluid collection device 1100. The two portions 1114*a*, 1114*b* of the second region 1114 are configured to fold towards the first region 1112 with the different adhesive strip 1152*a*, 1152*b* of each of the two portions 1114*a*, 1114*b* of the second region 1114 positioned to secure to the outer surface of the first region 1112 to position the fluid permeable layer 1110 proximate to the head of the penis 10. In the wrapped configuration on the penis 10, the conduit 108 extends through the slot 1118 into the chamber. The fluid permeable layer 1120 is positioned on the inner surface of the second region 1112 effective to direct urine discharged from the penis 10 to the conduit 108 when the fluid collection device 1100 is in the wrapped configuration shown in FIG. 11B.

Figure 12:
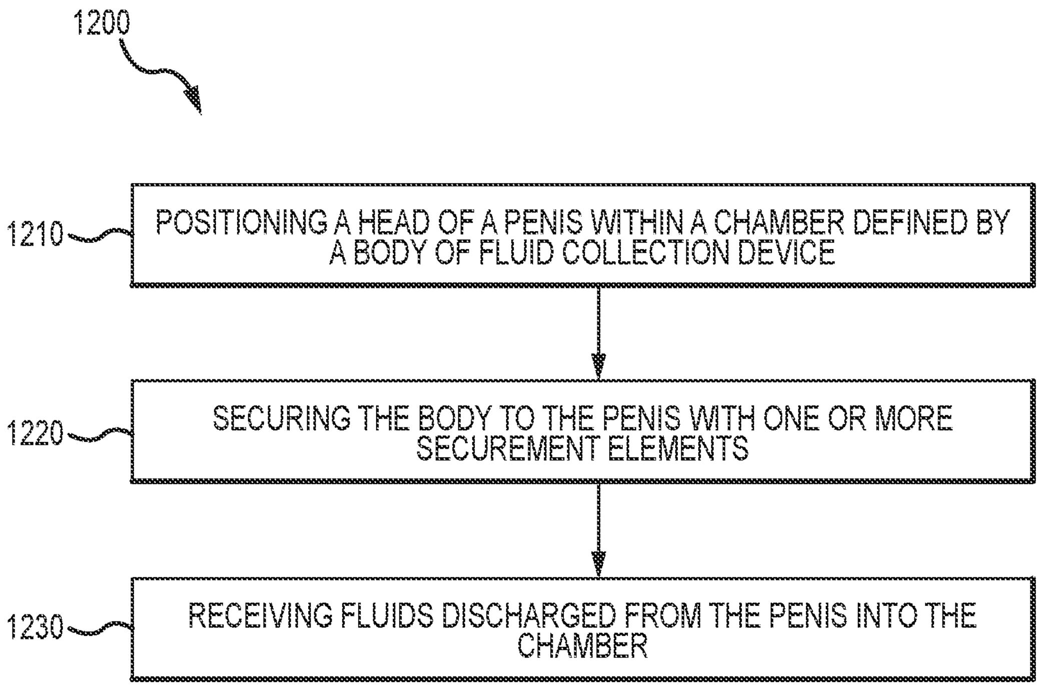
FIG. 12 is a flow diagram of a method to collect fluid, according to an embodiment.

FIG. 12 is a flow diagram of a method 1200 for collecting fluids, according to an embodiment. The method 1200 includes an act 1210 of positioning a head of a penis within a chamber defined by a body of a fluid collection device. The method 1200 also includes an act 1220 of securing the body of the fluid collection device to the penis with one or more securement elements. The method 1200 also includes an act 1230 of receiving fluids from the penis into the chamber of the fluid collection device. In some embodiments, the method 1200 includes an act of applying suction effective to suction the fluids from the chamber via a conduit disposed therein.

In some embodiments, the act 1210 of positioning a head of a penis of a user within a chamber defined by a body of fluid collection device includes inserting at least the head of the penis in the chamber of a tubular body of the fluid collection device 400 and rolling the tubular body onto the penis. The tubular body includes a fluid impermeable barrier housing a liquid or gel. The act 1220 of securing the body to the penis with one or more securement elements may then include securing a clip around the tubular body that stops or prevents the tubular body from rolling.

In some embodiments, the act 1210 of positioning a head of a penis of a user within a chamber defined by a body of fluid collection device includes inserting at least the head of the penis through at least one inflatable ring secured to the body in the fluid collection device 200. The act 1220 of securing the body to the penis with one or more securement elements may then include inflating the at least one inflatable ring to decrease an inner diameter of the at least one inflatable ring and secure the body to the penis.

In some embodiments, the act 1210 of positioning a head of a penis of a user within a chamber defined by a body of fluid collection device includes inserting at least the head of the penis through a tubular portion including an open cell foam and into a fluid impermeable cap secured to the tubular portion in the fluid collection devices 100, 600, 900. The act 1220 of securing the body to the penis with one or more securement elements may then include securing an adjustable strap around the tubular portion to secure the body to the penis when at least a portion of the penis is positioned within the chamber. The method 1200 may further include pulling the fluid in the chamber through the conduit with a vacuum force with air to flowing into chamber through the open cell foam.

In some embodiments, the act 1210 of positioning a head of a penis of a user within a chamber defined by a body of fluid collection device may include positioning the head of the penis within a chamber defined by a cup-shaped body with an open cell hydrophobic foam seal on a perimeter of the cup-shaped body of the fluid collection device 300 positioned against the user. The act 1220 of securing the body to the penis with one or more securement elements may then include positioning a support material of a jock strap garment over the cup-shaped body within one more bands of the jack strap garment wrapped around the user.

In some embodiments, the act 1210 of positioning a head of a penis of a user within a chamber defined by a body of fluid collection device may include wrapping a first region of the body of the fluid collection device 1100 around at least the head of the penis. The act 1220 of securing the body to the penis with one or more securement elements includes securing an adhesive strip on the inner surface of the first region to the outer surface of the first region, folding two portions of a second region of the body towards the first region and securing different adhesive strips on an inner surface of each of the two portions of the second region to the outer surface of the first region to position a fluid permeable layer on the two portions of the second region proximate to the head of the penis, the conduit extending through a slot between the two portions and into the chamber.

In some embodiments, the act 1220 of securing the body to the penis with one or more securement elements includes inflating one or more inflatable bags within the chamber of the fluid collection device 500. In some embodiments, the 1220 of securing the body to the penis with one or more securement elements includes tightening a drawstring secured to the body of the fluid collection device 700 around the penis. In some embodiments, the act 1220 of securing the body to the penis with one or more securement elements includes securing a hook and loop material fastener strap around a tubular portion of the body of the fluid collection device 800. In some embodiments, the act 1220 of securing the body to the penis with one or more securement elements includes tightening one or more worm drive hose clamps around a tubular portion of the body of the fluid collection device 1000.

Acts 1210, 1220, and 1230 of the method 1200 are for illustrative purposes. For example, the acts 1210, 1220, and 1230 of the method 120 may be performed in different orders, split into multiple acts, modified, supplemented, or combined. In an embodiment, one or more of the acts 1210, 1220, and 1230 of the method 120 may be omitted from the method 300. Any of the acts 1210, 1220, and 1230 of the method 120 may include using any of the fluid collection devices or systems disclosed herein.

Figure 13:
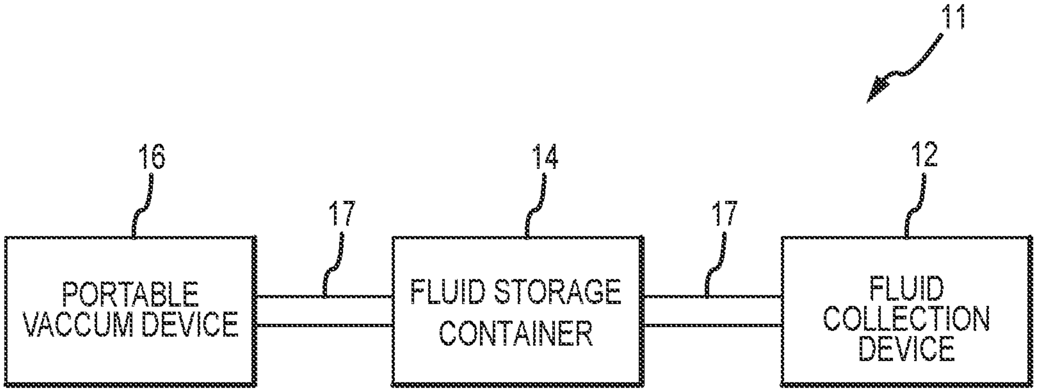
FIG. 13 is a block diagram of a system for fluid collection, according to an embodiment.

FIG. 13 is a block diagram of a system 11 for fluid collection, according to an embodiment. The system 11 includes a fluid collection device 12, a fluid storage container 14, and a portable vacuum source 16. The fluid collection device 12 may include any of the fluid collection devices described herein, such as the fluid collection devices 100, 200, 300, 400, 500, 600, 700, 800, 900, 1000, 1100. The fluid collection device 12, the fluid storage container 14, and the portable vacuum source 16 may be fluidly coupled to each other via one or more conduits 17. The conduit 17 may include any of the conduits described herein, such as the conduit 118. The fluid collection device 12 may be operably coupled to one or more of the fluid storage container 14 or the portable vacuum source via the conduit 17. Fluid (e.g., urine or other bodily fluids) collected in the fluid collection device 12 may be removed from the fluid collection device 12 via the conduit 17, which protrudes into an interior region of the fluid collection device 12. For example, a first open end of the conduit 17 may extend into the fluid collection device 12 to a reservoir therein. The second open end of the conduit 17 may extend into the fluid storage container 14 or the portable vacuum source 16. The suction force may be introduced into the interior region of the fluid collection device 12 via the first open end of the conduit 17 responsive to a suction (e.g., vacuum) force applied at the second end of the conduit 17. The suction force may be applied to the second open end of the conduit 17 by the portable vacuum source 16 either directly or indirectly.

The suction force may be applied indirectly via the fluid storage container 14. For example, the second open end of the conduit 17 may be disposed within the fluid storage container 14 and an additional conduit 17 may extend from the fluid storage container 14 to the portable vacuum source 16. Accordingly, the portable vacuum source 16 may apply suction to the fluid collection device 12 via the fluid storage container 14. The suction force may be applied directly via the fluid storage container 14. For example, the second open end of the conduit 17 may be disposed within the portable vacuum source 16. An additional conduit 17 may extend from the portable vacuum source 16 to a point outside of the fluid collection device 12, such as to the fluid storage container 14. In such examples, the portable vacuum source 16 may be disposed between the fluid collection device 12 and the fluid storage container 14.

The fluid collection device 12 may be shaped and sized to be positioned on a penis. The fluid collection device 12 may include body at least partially defining a chamber (e.g., interior region of the fluid collection device member) of the fluid collection device 12. The fluid collection member of the fluid collection device 12 may include a fluid permeable body disposed within the fluid impermeable barrier. The fluid permeable body may include a fluid permeable membrane and fluid permeable support disposed within the fluid permeable membrane. The conduit 17 may extend into the fluid collection device 12 at an end region of the fluid collection device 12. Example fluid collection devices for use with the systems and methods herein are described in more detail above.

In some embodiments, the fluid storage container 14 may include a bag (e.g., drainage bag), a bottle or cup (e.g., collection jar), or any other enclosed container for storing bodily fluids such as urine. In examples, the conduit 17 may extend from the fluid collection device 12 and attach to the fluid storage container 14 at a first point therein. An additional conduit 17 may attach to the fluid storage container 14 at a second point thereon and may extend and attach to the portable vacuum source 16. For example, the fluid storage container 14 may include a container fluidly coupled to a first conduit section that is also fluidly coupled to the fluid collection member of the fluid collection device 12. The container may be fluidly coupled to a second section of the conduit 17 that is also fluidly coupled to a portable vacuum source. In such examples, the portable vacuum source 16 may provide a vacuum/suction through the container to the fluid collection member to provide suction in the chamber of the fluid collection member. Accordingly, a vacuum (e.g., suction) may be drawn through fluid collection device 12 via the fluid storage container 14. As the fluid is drained from the chamber, the fluid may travel through the first section of conduit to the fluid storage container where it may be retained. Fluid, such as urine, may be drained from the fluid collection device 12 using the portable vacuum source 16.

In some embodiments, the portable vacuum source 16 may be disposed in or on the fluid collection device 12. In such examples, the conduit 17 may extend from the fluid collection device and attach to the portable vacuum source 16 at a first point therein. An additional conduit 17 may attach to the portable vacuum source 16 at a second point thereon and may extend out of the fluid collection device 12, and may attach to the fluid storage container 14. Accordingly, a vacuum (e.g., suction) may be drawn through fluid collection device 12 via the fluid storage container 14.

The portable vacuum source 16 may include one or more of a manual vacuum pump, and electric vacuum pump, a diaphragm pump, a centrifugal pump, a displacement pump, a magnetically driven pump, a peristaltic pump, or any pump configured to produce a vacuum. The portable vacuum source 16 may provide a vacuum or suction to remove fluid from the fluid collection member of the fluid collection device 12. In some embodiments, the portable vacuum source 16 may be powered by one or more of a power cord (e.g., connected to a power socket), one or more batteries, or even manual power (e.g., a hand operated vacuum pump). In examples, the portable vacuum source 16 may be sized and shaped to fit outside of, on, or within the fluid collection device 12. For example, the portable vacuum source 16 may include one or more miniaturized pumps or one or more micro pumps. The portable vacuum sources 16 disclosed herein may include one or more of a switch, a button, a plug, a remote, or any other device suitable to activate the portable vacuum source 16. It should be understood that the portable vacuum sources 16 disclosed herein may provide a portable means of providing a suction or vacuum that allows use of the devices and systems herein outside of hospital or care facility environments where vacuum lines are plumbed into patient rooms or large (e.g., larger or heavier than a patient can readily carry) vacuum sources are located. For example, a portable vacuum source may be small and light enough to be carried by a user (e.g., patient) or aid (e.g., nurse) during transportation of the user.

As used herein, the term “about” or “substantially” refers to an allowable variance of the term modified by “about” by ±10% or ±5%. Further, the terms “less than,” “or less,” “greater than”, “more than,” or “or more” include as an endpoint, the value that is modified by the terms “less than,” “or less,” “greater than,” “more than,” or “or more.”

While various aspects and embodiments have been disclosed herein, other aspects and embodiments are contemplated. The various aspects and embodiment disclosed herein are for purposes of illustration and are not intended to be limiting.

What is claimed is:

1. A male fluid collection device, comprising:

a body including a substantially tubular portion of an open cell foam and having a proximal end, a distal end, an inner surface at least partially defining a chamber sized to receive at least a head of a penis therein, an outer surface, and a plurality of projections extending inwardly from the inner surface, wherein some projections of the plurality of projections are spaced distally in the chamber from adjacent projections of the plurality of projections;

a conduit in fluid communication with the chamber, wherein at least a portion of the outer surface of the substantially tubular portion of the open cell foam forms an outer surface of the male fluid collection device effective to allow air to flow into the chamber through the open cell foam when a vacuum is pulled in the chamber through the conduit;

a fluid permeable material positioned within the chamber and configured to wick fluid discharged from the penis towards the conduit, the fluid permeable member being positioned and terminating distal to the plurality of projections; and an adjustable strap positioned and configured to tighten around the tubular portion to secure the body to the penis when at least a portion of the penis is positioned within the chamber, wherein the tubular portion has a C-shaped cross-section that has a slit or gap that is adjustable to a closed orientation to form an O-shaped cross-section when then the adjustable strap is tightened around the tubular portion, wherein the plurality of projections are sized and positioned to interface the head of the penis as the penis is inserted into the chamber, and are angled from the inner surface of the tubular portion towards the fluid permeable material before the penis contacts the plurality of projections such that a notch opening towards the fluid permeable material is formed between each projection of the plurality of projections and the inner surface of the tubular portion, wherein proximal projections of the plurality of projections that are proximal of adjacent distal projections of the plurality of projections extend distally past at least a portion of the adjacent distal projections.

2. The male fluid collection device of claim 1, wherein the body includes:

a fluid impermeable cap secured to the tubular portion and including an aperture distal to the tubular portion, the fluid impermeable cap and the tubular portion defining the chamber and the aperture being configured to receive the conduit effective to provide fluid communication between the chamber and the conduit;

wherein the tubular portion is secured to the fluid impermeable cap with the fluid impermeable cap terminating distal to the proximal end of the tubular portion such that the at least the portion of the outer surface of the substantially tubular portion of the open cell foam forms the outer surface of the male fluid collection device effective to allow air to flow into chamber through the open cell foam when a vacuum is pulled in the chamber through the conduit.

3. The male fluid collection device of claim 2, wherein:

the adjustable strap includes at least one of an elastic adjustable strap, a hose clamp, a hook and loop fastener material, or one or more fasteners; and the tubular portion includes a shore A durometer of less than about 20.

4. The male fluid collection device of claim 2, wherein the fluid permeable material is secured to the fluid impermeable cap within the chamber.

5. The male fluid collection device of claim 1, wherein the body includes a fluid impermeable cap secured to the tubular portion and including an aperture distal to the tubular portion, the fluid impermeable cap and the tubular portion defining the chamber and the aperture being configured to receive the conduit effective to provide fluid communication between the chamber and the conduit.

6. The male fluid collection device of claim 5, wherein:

the adjustable strap includes at least one of an elastic adjustable strap, a hose clamp, a hook and loop fastener material, or one or more fasteners;

the tubular portion includes an elastomeric material;

the plurality of projections have a shore A durometer of about 30 to about 60 and include one or more of an elastomer, a silicone, a thermoplastic elastomer, or thermoplastic polyurethane.

7. The male fluid collection device of claim 1, wherein:

the body includes a fluid impermeable cap secured to the tubular portion and including an aperture distal to the tubular portion, the fluid impermeable cap and the tubular portion defining the chamber and the aperture being configured to receive the conduit effective to provide fluid communication between the chamber and the conduit; and the adjustable strap includes a hook and loop material fastener strap positioned and configured to tighten around the tubular portion to secure the body to the penis when at least a portion of the penis is positioned within the chamber.

8. The male fluid collection device of claim 1, wherein:

the body includes a fluid impermeable cap secured to the tubular portion and including an aperture distal to the tubular portion, the fluid impermeable cap and the tubular portion defining the chamber and the aperture being configured to receive the conduit effective to provide fluid communication between the chamber and the conduit; and the adjustable strap includes one or more worm drive hose clamps positioned and configured to tighten around the tubular portion to secure the body to the penis when at least a portion of the penis is positioned within the chamber.

9. The male fluid collection device of claim 1, further comprising:

a fluid impermeable cap secured to the tubular portion and including an aperture distal to the tubular portion; and the fluid permeable material is secured to the fluid impermeable cap within the chamber and a reservoir of void space is positioned in the fluid impermeable cap between the fluid permeable material and the aperture, wherein the fluid permeable material is configured to wick fluid discharged from the penis into the reservoir and towards the conduit.

10. The male fluid collection device of claim 1, wherein the adjustable strap includes at least one of an elastic adjustable strap, a hose clamp, a hook and loop fastener material, or one or more fasteners.

11. A method of collecting fluid from a male, the method comprising:

inserting at least a head of a penis of a user within a chamber defined by a tubular portion of an open cell foam of a body of a fluid collection device to interface a plurality of projections extending inwardly from an inner surface of the tubular portion, some projections of the plurality of projections spaced distally in chamber from adjacent projections of the plurality of projections, wherein the plurality of projections are angled from the inner surface of the tubular portion towards the fluid impermeable cap before the penis contacts the plurality of projections such that a notch opening towards the fluid impermeable cap is formed between each projection of the plurality of projections and the inner surface of the tubular portion, thereby inhibiting the fluid collection device from moving out of position on the penis;

securing the body to the penis by tightening an adjustable strap around the body, thereby adjusting from a C-shaped cross-section having a slit or gap to a closed orientation having an O-shaped cross-section;

receiving fluids discharged from the penis into the chamber of the fluid collection device; and pulling the fluid in the chamber through a conduit with a vacuum force applied to the conduit, the tubular portion of the open cell foam including an outer surface that at least partially forms an outer surface of the fluid collection device such that air flows into chamber through the open cell foam, wherein the fluid collection device includes a fluid permeable material positioned within the chamber that wicks the fluids discharged from the penis towards the conduit, the fluid permeable member being positioned and terminating distal to the plurality of projections.

12. The method of claim 11, wherein securing the body to the penis includes securing a hook and loop material fastener strap around a tubular portion of the body.

13. The method of claim 11, wherein securing the body to the penis includes tightening one or more worm drive hose clamps around a tubular portion of the body.

14. The method of claim 11, further comprising removing the fluid collection device from the penis by pinching the tubular portion, thereby separating a portion of the plurality of projections from the penis.

15. A male fluid collection device, comprising:

a body including a substantially tubular portion of an open cell foam and having a proximal end, a distal end, an inner surface at least partially defining a chamber sized to receive at least a head of a penis therein, and an outer surface;

a conduit in fluid communication with the chamber, wherein at least a portion of the outer surface of the substantially tubular portion of the open cell foam forms an outer surface of the male fluid collection device effective to allow air to flow into the chamber through the open cell foam when a vacuum is pulled in the chamber through the conduit;

a fluid permeable material positioned within the chamber and configured to wick fluid discharged from the penis towards the conduit, the fluid permeable member being positioned and terminating at least proximate to the distal end of the body; and an adjustable strap positioned and configured to tighten around the tubular portion to secure the body to the penis when at least a portion of the penis is positioned within the chamber.

16. The male fluid collection device of claim 15, wherein the body includes:

a fluid impermeable cap secured to the tubular portion and including an aperture distal to the tubular portion, the fluid impermeable cap and the tubular portion defining the chamber and the aperture being configured to receive the conduit effective to provide fluid communication between the chamber and the conduit;

wherein the tubular portion is secured to the fluid impermeable cap with the fluid impermeable cap terminating distal to the proximal end of the tubular portion such that the at least the portion of the outer surface of the substantially tubular portion of the open cell foam forms the outer surface of the male fluid collection device effective to allow air to flow into chamber through the open cell foam when a vacuum is pulled in the chamber through the conduit.

17. The male fluid collection device of claim 16, wherein:

the adjustable strap includes at least one of an elastic adjustable strap, a hose clamp, a hook and loop fastener material, or one or more fasteners; and the tubular portion includes a shore A durometer of less than about 20.

18. The male fluid collection device of claim 16, wherein the fluid permeable material is secured to the fluid impermeable cap within the chamber and configured to wick fluid discharged from the penis towards the conduit.

19. The male fluid collection device of claim 15, wherein the body includes a fluid impermeable cap secured to the tubular portion and including an aperture distal to the tubular portion, the fluid impermeable cap and the tubular portion defining the chamber and the aperture being configured to receive the conduit effective to provide fluid communication between the chamber and the conduit.

20. The male fluid collection device of claim 19, wherein:

the adjustable strap includes at least one of an elastic adjustable strap, a hose clamp, a hook and loop fastener material, or one or more fasteners; and the tubular portion includes an elastomeric material.

21. The male fluid collection device of claim 15, wherein the tubular portion has a C-shaped cross-section that has a slit or gap that is adjustable to a closed orientation to form an O-shaped cross-section when then the adjustable strap is tightened around the tubular portion.

22. The male fluid collection device of claim 15, wherein the body includes a plurality of projections extending inwardly from an inner surface, the plurality of projections being sized and positioned to interface the head of the penis as the penis is inserted into the chamber and being angled from the inner surface of the towards the distal end such that proximal projections of the plurality of projections that are proximal of adjacent distal projections of the plurality of projections extend distally past at least a portion of the adjacent distal projections.

* * * * *